United States Patent [19]
Ensminger et al.

[11] Patent Number: 5,356,381
[45] Date of Patent: * Oct. 18, 1994

[54] IMPLANTABLE ACCESS DEVICES

[76] Inventors: William D. Ensminger, 2770 Parkridge Dr.; James A. Knol, 1059 Hasper; James C. Andrews, 3568 River Pines, all of Ann Arbor, Mich. 48103

[*] Notice: The portion of the term of this patent subsequent to Oct. 15, 2008 has been disclaimed.

[21] Appl. No.: 158,042

[22] Filed: Nov. 24, 1993

Related U.S. Application Data

[63] Continuation of Ser. No. 940,444, Sep. 4, 1992, abandoned, which is a continuation-in-part of Ser. No. 818,626, Jan. 10, 1992, Pat. No. 5,226,879, which is a continuation-in-part of Ser. No. 654,661, Feb. 15, 1991, Pat. No. 5,180,365, which is a continuation-in-part of Ser. No. 539,793, Jun. 18, 1990, Pat. No. 5,053,013, which is a continuation-in-part of Ser. No. 487,541, Mar. 1, 1990, Pat. No. 5,057,084.

[51] Int. Cl.$^5$ ............................................. A61M 11/00
[52] U.S. Cl. ........................................ 604/93; 604/181
[58] Field of Search .......... 604/93, 181, 183, 245-249, 604/256, 257

[56] References Cited

U.S. PATENT DOCUMENTS

| | | |
|---|---|---|
| 3,288,137 | 1/1964 | Lund . |
| 3,402,710 | 9/1968 | Paleschuck . |
| 3,565,078 | 2/1971 | Vaillancourt et al. . |
| 3,699,956 | 10/1972 | Kitrilakis et al. . |
| 4,181,132 | 1/1980 | Parks . |
| 4,190,040 | 2/1980 | Schulte . |
| 4,230,109 | 10/1980 | Geiss . |
| 4,256,102 | 3/1981 | Monaco . |
| 4,387,879 | 6/1983 | Tauschinski . |
| 4,405,320 | 9/1983 | Cracauer, Jr. et al. . |
| 4,425,119 | 1/1984 | Berglund . |
| 4,430,081 | 2/1984 | Timmermans . |
| 4,439,188 | 3/1984 | Dennehey et al. . |

(List continued on next page.)

FOREIGN PATENT DOCUMENTS

| | | |
|---|---|---|
| 0119596 | 3/1984 | European Pat. Off. . |
| 134745 | 8/1984 | European Pat. Off. . |
| 3242870 | 6/1983 | Fed. Rep. of Germany . |
| 3528878 | 2/1987 | Fed. Rep. of Germany . |
| 1296652 | 5/1962 | France . |
| 8300367 | 2/1983 | PCT Int'l Appl. . |
| 2192338 | 1/1988 | United Kingdom . |

OTHER PUBLICATIONS

Rational Drug Therapy, May 1988, vol. 22, No. 5, William D. Ensminger M.D. and Ira S. Wollner, M.D.

*Primary Examiner*—John D. Yasko

[57] ABSTRACT

An access port (10) for implantation adapted for providing repeated access to specific tissue within a patient and communicating with the tissue by an internal implanted catheter (52). The access ports according to this invention incorporate an enlarged entrance orifice (13) with a funnel shaped internal cavity that narrows down to a reduced diameter passageway (18). An articulating catheter valve (24) is provided within the passageway which normally prevents the flow of fluids through the valve but which can be penetrated by an external introduced filament (32) such as a catheter. After implantation, an external filament (32) is introduced into the port (10) and guided by the passageway into registry with the catheter valve (24). Continued feeding of the filament (32) causes the filament to pass through the valve (24). Thereafter, with a catheter (32) inserted, therapeutic agents can be infused into the patient, or body fluids can be withdrawn. Alternate embodiments disclose various valve concepts (56) and means for providing a change in direction of an introduced filament inserted through the access device. Additional embodiments disclose the concepts of providing an antimicrobial fluid bath (98) within the device for prevention of infection and various approaches for securely connecting an internal catheter (52) to an access port.

50 Claims, 16 Drawing Sheets

U.S. PATENT DOCUMENTS

| | | |
|---|---|---|
| 4,447,237 | 5/1984 | Frisch et al. . |
| 4,464,178 | 10/1984 | Dalton . |
| 4,490,137 | 12/1984 | Moukheibir . |
| 4,491,126 | 1/1985 | Cullor . |
| 4,534,759 | 8/1985 | Trawöger . |
| 4,543,088 | 9/1985 | Bootman et al. . |
| 4,547,194 | 10/1985 | Moorehead . |
| 4,569,675 | 2/1985 | Prosl et al. . |
| 4,578,061 | 3/1985 | Lemelson . |
| 4,578,063 | 3/1986 | Inmann et al. . |
| 4,581,020 | 4/1986 | Mittleman . |
| 4,623,329 | 11/1985 | Drobish et al. . |
| 4,634,422 | 1/1987 | Kantrowitz et al. . |
| 4,645,495 | 2/1987 | Vaillancourt . |
| 4,650,473 | 3/1987 | Bartholomew et al. . |
| 4,673,394 | 6/1987 | Fenton, Jr. et al. . |
| 4,682,981 | 7/1987 | Suzuki et al. . |
| 4,692,146 | 9/1987 | Hilger . |
| 4,695,273 | 9/1987 | Brown . |
| 4,704,103 | 11/1987 | Stober et al. . |
| 4,710,167 | 12/1987 | Lazorthes . |
| 4,710,174 | 12/1987 | Moden et al. . |
| 4,712,583 | 12/1987 | Pelmulder et al. . |
| 4,781,680 | 11/1988 | Redmond et al. . |
| 4,781,693 | 11/1988 | Martinez et al. . |
| 4,781,695 | 11/1988 | Dalton . |
| 4,790,826 | 12/1988 | Elftman . |
| 4,810,241 | 3/1989 | Rogers . |
| 4,832,054 | 5/1989 | Bark . |
| 4,842,591 | 6/1989 | Luther . |
| 4,857,053 | 8/1989 | Dalton . |
| 4,857,062 | 4/1989 | Russell . |
| 4,886,501 | 12/1989 | Johnston et al. . |
| 4,929,235 | 5/1990 | Merry et al. . |
| 4,978,338 | 12/1990 | Melsky . |
| 5,041,098 | 8/1991 | Loiterman et al. . |

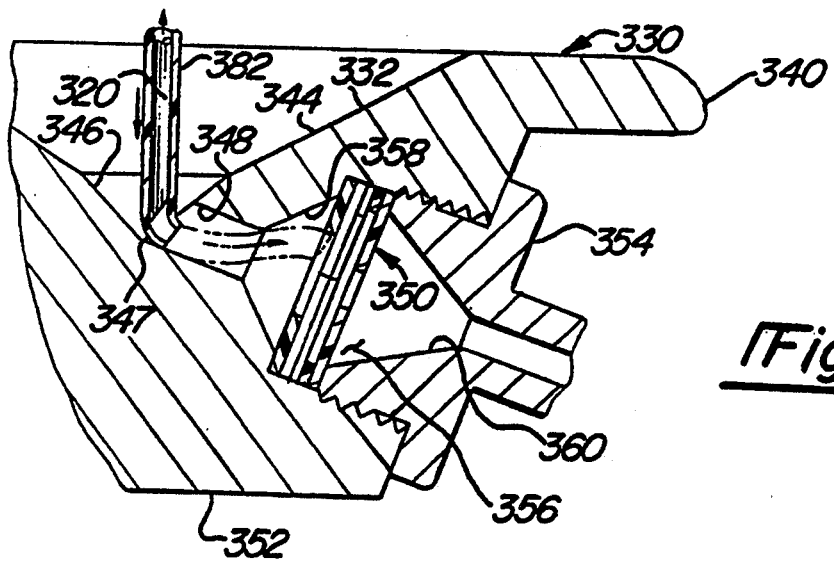
*Fig-36*
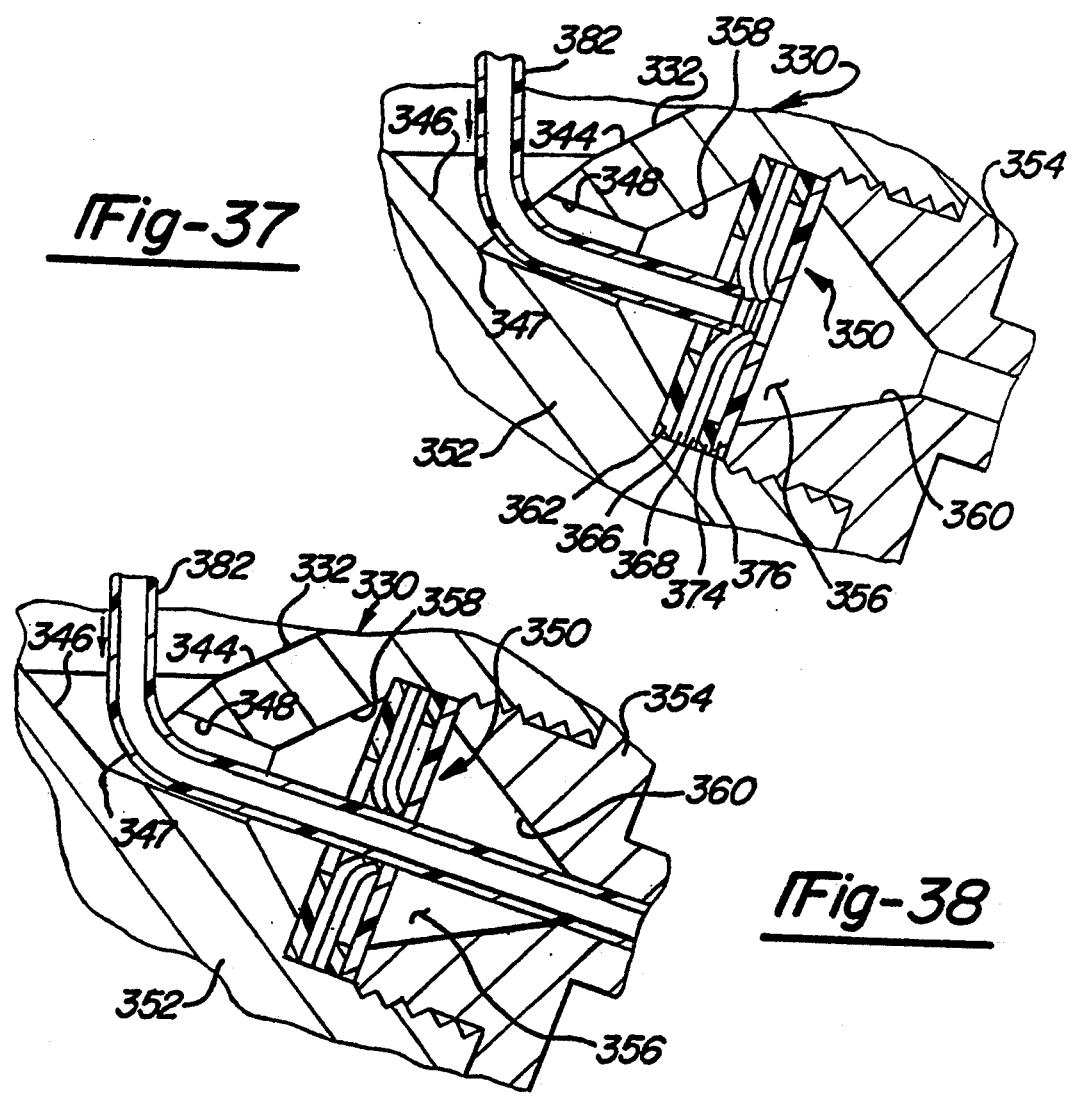
*Fig-37*
*Fig-38*

IMPLANTABLE ACCESS DEVICES

CROSS REFERENCE TO RELATED APPLICATIONS

This application is a continuation of U.S. application Ser. No. 07/940,444 filed Sep. 4, 1992 now abandoned which is a continuation-in-part of U.S. application Ser. No. 818,626 filed on Jan. 10, 1992, entitled "Implantable Infusion Device" now U.S. Pat. No. 5,226,879 which is a continuation-in-part of U.S. application Ser. No. 654,661 filed on Feb. 15, 1991, now U.S. Pat. No. 5,180,365 which is a continuation-in-part of U.S. application Ser. No. 539,793 filed on Jun. 18, 1990 now issued U.S. Pat. No. 5,053,013, which is a continuation-in-part of U.S. application Ser. No. 487,541 filed on Mar. 1, 1990 now issued U.S. Pat. No. 5,057,084.

FIELD OF THE INVENTION

This invention relates to devices for introducing a filament, such as a catheter, into a patient for infusing a therapeutic agent to a desired site or withdrawing a fluid from the patient. More particularly, the invention relates to an access port which is implanted such that no portion is transcutaneous. The access port is subcutaneous but designed so as to facilitate repeated access by the percutaneous route.

BACKGROUND AND SUMMARY OF THE INVENTION

In current human and animal medical practice, there are numerous instances where therapeutic agents must be delivered to a specific organ or a tissue within the body. An example is the infusion of chemotherapy into a central vein on a recurring basis over a lengthy treatment period for widespread sites of malignant tumor. Without an access device for intravenous drug infusion, multiple vein punctures over a lengthy period would result in progressive thrombosis, venous sclerosis, and destruction of small diameter peripheral vessels. In other cases, it may be desirable to infuse chemotherapy to a localized malignant tumor site. It may be difficult or impossible to deliver an agent specifically to such a site on a regular repetitive basis without surgically implanting an access system. Similarly, repeated arterial access is occasionally needed for injection of an X-ray dye or contrast agent into an artery for diagnostic purposes. In other situations, there is a need to repetitively remove a body fluid for analysis from a remote body site. Finally, sensing and physiological measuring devices incorporated into small diameter catheters and small diameter optical fibers are increasingly being utilized for monitoring body processes and could be more easily implemented through a properly designed access device with an adequate internal diameter.

In prior medical practice, percutaneous catheters have been used to provide vascular or organ access for drug therapy or the withdraw of body fluids. Although such systems generally performed in a satisfactory manner, numerous problems were presented by such therapy approaches, including the substantial care requirements of the patients, e.g. dressing changes with sterile techniques, a significant rate of infection of the catheter because of its transcutaneous position, and a high rate of venous thrombosis, particularly if the catheter was located within an extremity vein.

Implantable infusion devices or "ports" have recently become available and represent a significant advance over transcutaneous catheters. Presently available infusion ports have a number of common fundamental design features. The ports themselves comprise a housing which forms a reservoir that can be constructed from a variety of plastic or metal materials. A surface of the reservoir is enclosed by a high-density, self-sealing septum, typically made of silicone rubber. Connected to the port housing is an internal catheter which communicates with a vein or other site within the patient where the infusion of therapeutic agents is desired. Implantation of such devices generally proceeds by making a small subcutaneous pocket in an appropriate area of the patient under local anesthesia. The internal catheter is tunneled to the desired infusion site. When the care provider desires to infuse or remove materials through the port, a hypodermic needle is used which pierces the skin over the infusion port and is placed into the port.

Although the presently available implantable infusion ports generally operate in a satisfactory manner, they have a number of shortcomings. Since these devices rely on a compressed rubber septum for sealing and since large diameter needles can seriously damage the septum, there are limitations in the diameter of needles which can be used to penetrate the septum. Also, the needles are randomly inserted to penetrate the septum, producing a cut or puncture wound, partially consuming and destroying the septum with each penetration. The diameter limitations severely restrict the flow rate of fluids passing through the port. In cases where it is desirable to infuse drugs using a flexible external catheter, the catheter must be fed through the needle that penetrates the septum. Such catheters have an extremely small inside diameter and, therefore, impose severe limitations on fluid flow rate.

During prolonged infusion using a conventional port, the infusion needle is taped to the patients skin to hold it in position. Conventional ports do not allow the needle to penetrate deeply into the port. Because of this, a small displacement of the needle can cause it to be pulled from the port. In cases where locally toxic materials are being infused, extravasation of such materials can cause local tissue damage which may require corrective surgery such as skin grafting or removal of tissue.

Presently available implantable drug infusion devices also have a significant size to provide an acceptable target surface area for the care provider who must locate the port and penetrate the septum with a needle. The port housing becomes bulky as the septum size increases since structure is required to maintain the septum in compression to provide self-sealing after the needle is removed. Moreover, presently available infusion ports are difficult to clear if thrombosis occurs within the port or within the implanted internal catheter since it is difficult, if not impossible, to feed a cleaning wire through the penetrating hypodermic needle in a manner which will clear the infusion device and the internal catheter. Present infusion ports also have a retained volume beneath the self-sealing septum which increases the volume of drug which must be administered to enable a desired quantity to reach the infusion site. This retained volume also poses problems when a care provider desires to successively deliver multiple drugs to the same infusion site which are incompatible when mixed. Additionally, when it is desired to withdraw blood through the port, the retained volume of the prior art infusion ports comprises an area where blood clotting can occur, thus interfering with future access to the site. And finally, for present infusion ports, there is a risk that the care provider attempting to pierce the port septum will not properly enter it, leading to the possibility of extravasation which can cause significant undesirable consequences as mentioned above.

The present invention relates to a family of implantable access ports which provide numerous enhancements over prior art devices. In accordance with this invention, an access port is provided which incorporates the funnel-shaped entrance orifice which narrows down to a reduced diameter passageway. The passageway retains a valve. One characteristic of valves used with the present invention is that the valves are not physically damaged or destroyed by the passage of a filament through the valve. In this regard, the valve can be referred to as being a "non-destructive" valve. Another characteristic of the valves intended to be used with the present invention is that they are constructed to be repetitively engaged by the filament in a predetermined location. Generally, this location is the center of the valve. Valves which meets the above criteria are referred to as "articulating catheter valves" or "articulating valves", such as a multi-element leaflet valve assembly. After the valve, the passageway is connected to an implanted internal catheter.

Several embodiments of this invention are intended to be used by inserting an instrument such as a needle, trocar or other introducer through the skin into a port entrance orifice which introduces a filament, such as a catheter, into the port. While some embodiments of this invention are used with blunt introducers, other embodiments of the present invention are adapted to be used in conjunction with a sharp hypodermic access needle of conventional design which may be used by itself for infusion or fluid withdrawal, or with an external catheter having the needle fed through it (or vise versa) allowing the catheter to be put in position within the access port or fed into the implanted catheter for infusion or withdrawal of fluid. The entrance orifice has a hard surface which guides the needle to a guide passageway. The reduced diameter guide passageway of the port housing can be used to accurately align the access needle and/or catheter to strike the articulating valve at a desired area. In this manner, a needle can be used to pass through the catheter valve repeatedly without damaging the function of the valve.

According to another group of embodiments of this invention, additional features of access ports are described. One area of potential improvement for some purposes is the provision of a port designed for implantation in a patient's arm which has an access passageway for an inserted needle. The body of this port is slightly angled upward to facilitate access. Such an angled access port can also feature modifications to the entrance orifice to again further enhance the ability to access the implanted port. This application further describes a valving concept for an implanted port which provides a high degree of resistance to body fluid leakage through the port and which further provides a relatively low level of friction upon insertion of an external catheter and a relatively higher degree of friction upon withdrawal of the catheter. This difference in resistance aids both in inserting of the catheter and in maintaining the catheter in an inserted condition within the implanted port.

This specification also describes port design features which are best embodied in a port in which the entrance funnel is in a plane generally parallel to the mounting base of the port (i.e. the accessing needle penetrates perpendicular to the mounting base). One improvement for such ports is the provision of a physical feature such as a projecting lug, flange or other protuberance which enables the clinician to determine the orientation of the implanted port through tactile examination. By knowing the port orientation, the needle and introduced filament can often be more readily inserted into the port. This series of ports, known as "chest wall" ports (named for a preferred usage), also feature a funnel-shaped entrance orifice having a progressively changing included angle. The orifice starts at its outer periphery with a relatively shallow included angle which increases toward the port's center. This progressive change in cone angle provides two significant benefits. First, it results in a port which has a relatively shallow funnel that reduces the distance between the skin surface and the catheter valve which seals around the introduced catheter or the filament and which also serves to better orient and hold the introduced needle.

Several of the ports according to this specification also feature means for stopping the introduced needle before it reaches the catheter valve but which permits the introduced catheter to pass through the catheter valve.

The access ports in accordance with additional embodiments of this invention achieve simplicity in construction and reduce the number of components required to provide the necessary fluid seal. In those applications where it is desired to access a port using a sharp needle, damage to elastomeric sealing elements in prior port designs can occur over repeated entries to the port. In accordance with these embodiments, the implanted port has an articulating valve mechanism in which the accessing needle (or other filament) contacts a hard material, such as a metal, to open the valve. Therefore, a durable device is provided which is not damaged through long term use. The features of this embodiment are achieved through the use of an articulating valve assembly in which a sealing element is normally maintained in contact with a valve seat. When introducing an external filament, which may be a needle, catheter, wire, optical fiber etc., the filament engages the sealing element forcing it from engagement with the valve seat. Once fully inserted into the access device, features are provided to assure a fluid seal around the introduced filament.

The access ports of this invention are implanted in the same general manner as prior art devices. When the care provider desires to infuse a therapeutic agent, remove a body fluid, or have vascular access, a filament such as a catheter is introduced into the port. The entrance orifice guides the introduced catheter or needle into a proper "docking" position with the articulating valve. By pushing on the externally introduced filament, the filament is forced through the valve, thereby providing an open communication pathway for the infusion of therapeutic agents, extraction of body fluids, introduction of an optical fiber, clearing by a wire, etc. The introduced filament can be fed into the internal catheter to any extend desired. In the case of introducing a flexible catheter, a guide wire can be inserted into the external catheter to increase its rigidity. The convenient access to the port and internal catheter enables these elements to be cleared with a clearing wire avoiding the problem of permanent impaction as seen in prior art devices. In addition, the ability to feed a guide wire into the access port and internal catheter of this invention enables the internal catheter to be repositioned using a bent or "steerable" guide wire.

The access ports having an articulating valve of this invention possess the advantage that they have a very small reservoir or "dead space", meaning that virtually all of the infused fluid is put through to the desired infusion site. This invention, therefore, facilitates infusion of incompatible materials in a serial fashion since very little of the previously infused fluid remains in the device when a subsequent infusion is carried out. This invention also facilitates simultaneous infusion of incompatible materials by using a multi-lumen catheter inserted through the implanted catheter.

Another aspect of the present invention is a design for an access port which is configured such that a line normal to the plane formed by the entrance orifice is nearly at a right angle to the exit passageway. The port access opening guides an introduced filament toward and into the internal catheter. This approach of guiding a catheter to undergo a bend through the port can be used with conventional port designs having a self-sealing rubber septum. Other aspects of the present invention relate to providing a reservoir within an access port for containing an antimicrobial (or antibacterial) fluid, offering enhanced protection against introduced infection. This invention is further related to various means of securely fastening an internal catheter to an access port.

Additional benefits and advantages of the present invention will become apparent to those skilled in the art to which this invention relates from the subsequent description of the preferred embodiments and the appended claims, taken in conjunction with the accompanying drawings.

BRIEF DESCRIPTION OF THE DRAWINGS

FIG. 36 is a partial cross-sectional view showing the accessing needle and catheter being more fully inserted into the port.

FIG. 37 is a partial cross-sectional view showing the introduced catheter penetrating the valve of the port.

FIG. 38 is a partial pictorial view showing an introduced catheter completely passing through the articulating valve and in a proper docking position with the port for material infusion.

DETAILED DESCRIPTION OF THE PREFERRED EMBODIMENTS

Figure 1:
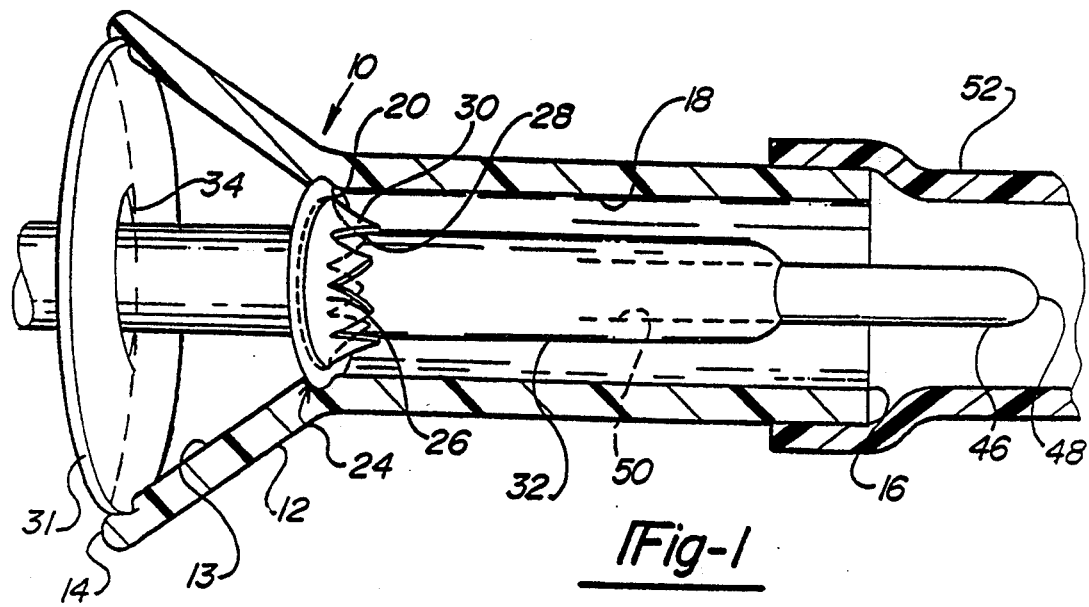
FIG. 1 is a cross-sectional view of an access port in accordance with a first embodiment of the present invention shown with an external catheter and obturator inserted though a leaflet type catheter valve.

An access port in accordance with a first embodiment of this invention is shown in FIG. 1 and is generally designated there by reference number 10. Access port 10 generally comprises housing 12 defining an entrance orifice 14, an inside cavity 13 which funnels down to base 20, with an exit orifice 16, and an elongated passageway 18 extending between the external orifice base, and exit orifice 16. In the embodiment shown, access port housing 12 is rotationally symmetrical about a central longitudinal axis passing through passageway 18 and an exit orifice 16, with which it is concentric. As is evident from FIG. 1, the conical entrance orifice 14 has a circular perimeter and has a diameter which is preferably several times greater than the internal diameter of passageway 18 (i.e. an area difference of four times or more). The entire housing 12 can be formed in one piece from numerous polymeric materials or metals which are compatible with human or animal implantation.

Positioned within passageway 18, substantially adjacent to the entrance orifice 14, is an articulating valve assembly. The valve normally remains closed and provides resistance to the flow of fluids through the passageway. However, the valve will permit a filament to pass through it and communicate with an internal catheter as further discussed below. The valve is of a type which is not destroyed or physically damaged by the passage of the filament through it. Another characteristic of the articulating valve used in this and other embodiments is that the valve is designed for repetitive engagement by the filament in a predetermined location.

Figure 4:
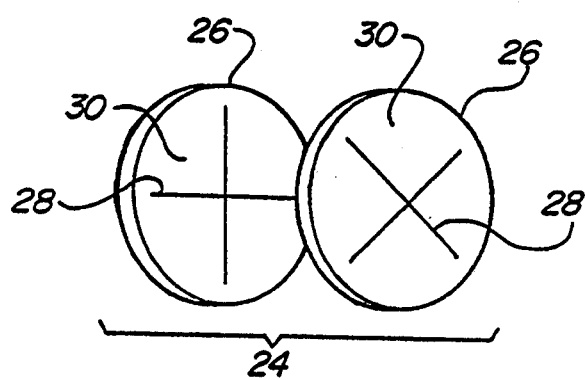
FIG. 4 is a pictorial view of the leaflet valve used with the access port of FIG. 1.

One such articulating valve is a leaflet valve assembly 24, which is also shown in an exploded fashion in FIG. 4. Leaflet valve assembly 24 is comprised of one or more thin elastic disks 26 made, for example, from silicone rubber having one or more radial slits 28 cut through them. In development of the access port 10 of this invention, Applicants have found that a preferred disk 26, providing the desired characteristics for the valve assembly 24, is made from surgical silicone rubber and exhibits a hardness number of 27, Shore A, and has a thickness of 0.040 inches.

In the embodiment shown in FIGS. 1 and 4, two disks 26 are provided, each having two slits with a right angle between them so that each defines four leaves 30. The disks 26 are oriented and stacked against one another so that slits 28 of both the disks are angularly misaligned. This misalignment is intentionally provided to enhance the sealing characteristics of valve assembly 24 when it is in its normal closed position, as shown in FIG. 4. Numerous other configurations for valve disk 26 can be provided, such as those incorporating any number of slits and thus having various numbers of leaves.

The embodiment of access port 10 shown in FIG. 1 includes an optional thin rubber septum 31 which acts to shield entrance orifice 14. When a foreign object is implanted in a human, the body often develops fibrous tissue around the object. If an exposed concave pocket is present, such as an open entrance orifice 14, the pocket could possibly become filled with such fibrous tissue. The development of this tissue, should such occur in a patient, might restrict access into the port, and potentially could interfere with the catheter valve function. Therefore, septum 31 provided which is pre-slit at 34 to allow the introduced external filament to easily penetrate the septum. Septum 31 does not, however, provide a fluid-tight barrier as in prior art access port which have self-sealing characteristics and is easily penetrated by an accessing instrument. The provision of septum 31 prevents tissue growth inside the housing cavity and also enables the region of housing between entrance orifice 14 and leaflet valve assembly 24 to act as a reservoir for the retention of an antimicrobial fluid which aids in preventing the invasion of infectious agents during the use of access port 10.

Figure 2:
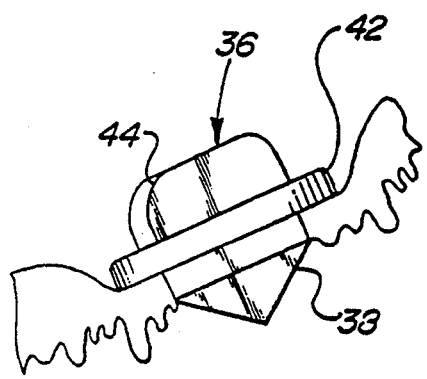
FIG. 2 is a pictorial view of a skin punch which may be used to make an incision into a patient's skin to permit insertion of an external catheter.
Figure 3:
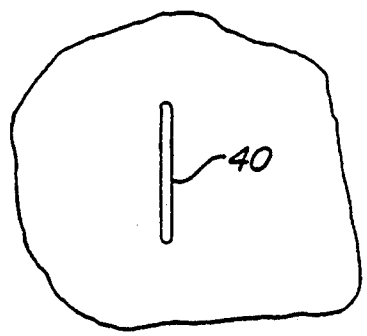
FIG. 3 is an illustration of a stab wound formed by the skin punch shown in FIG. 2.

In use, access port 10 is surgically positioned subcutaneously within the patient and mounted to suitable support tissue using conventional mounting techniques including sutures or surgical staples. While it is believed that the invention will be mostly readily mounted using fasteners such as sutures and staples, other subcutaneous mounting methods, specifically lacking fasteners, could also be employed. Internal catheter 52 is tunneled to the desired site in the body. When access is desired for the access of therapeutic agents, for the sampling of body fluids or for the introduction of physiological sensing elements (electrical or optical transducers, etc), a flexible external catheter 32 (or other filament) is introduced into access port 10, as shown in FIG. 1. Insertion of external catheter 32 can be facilitate using skin punch 36 as shown in FIG. 2. Skin punch 36 includes a pointed flat blade 38 having a width sufficient to make a desired length of an incision 40 shown in FIG. 3. Skin punch 36 includes a radially extending flange 42 which limits the depth of the incision 40. Tab 44 provides a convenient means for holding and using skin punch 36. Once external catheter 32 is introduced through stab wound 40, it passes into entrance orifice 14 and is guided by the funnel shaped configuration of the housing cavity into orientation with leaflet valve assembly 24. Continued insertion of external catheter 32 causes the external catheter to penetrate leaflet valve assembly 24, causing deflection (i.e. "articulation") of valve leaves 30.

In cases where external catheters 32 are used which are quite flexible, it is necessary to provide localized stiffening of the introduced catheter to facilitate its introduction through the stab wound and into the proper docking position with leaflet valve assembly 24. For such cases, a semi-rigid guide wire or obturator 46 having a blunt end 48 can be used which is inserted through the internal passageway 50 of catheter 32.

Leaflet valve assembly 24 is relatively insensitive to the use of various diameters of external catheter 32, thus providing flexibility for the care provider. Furthermore, the characteristics of leaflet valve assembly 24 are such that once external catheter 32 is inserted through the valve, the valve does not exert a large radially inward compressive force on the catheter, thus preventing collapsing of the catheter which would seal off internal passageway 50. However, it does provide sufficient friction on the external catheter to stabilize its position.

Figure 5:
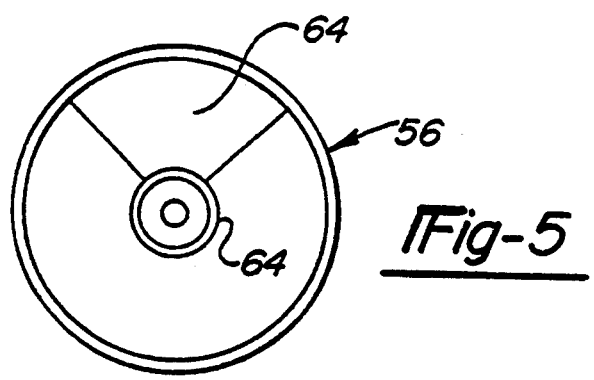
FIG. 5 is a frontal view of a cup type catheter valve which is an alternate embodiment of an articulating catheter valve.
Figure 6:
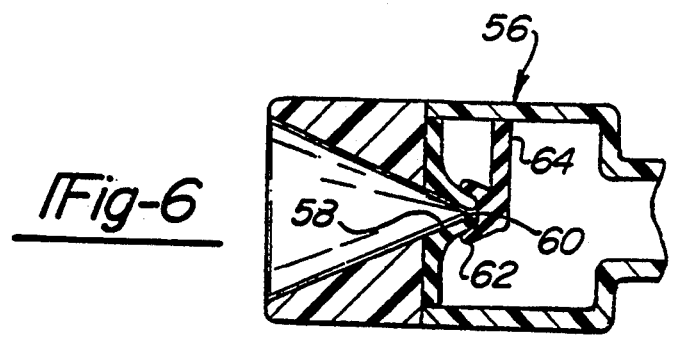
FIG. 6 is a cross-sectional view of the valve of FIG. 5 shown in a closed position.
Figure 7:
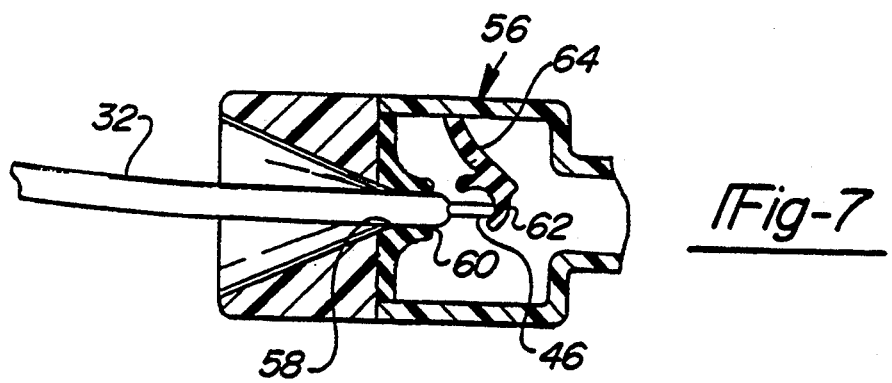
FIG. 7 is a cross-sectional view from FIG. 5 showing the catheter valve in a partly open position.
Figure 8:
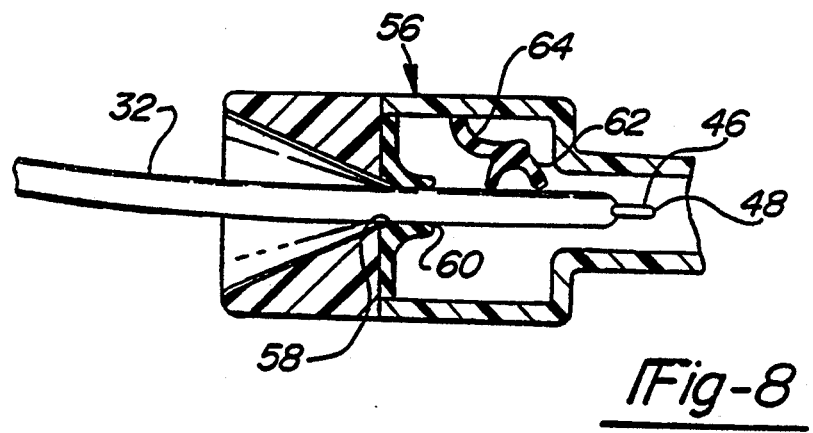
FIG. 8 is a sectional view taken from FIG. 5 showing the catheter valve in a fully open position permitting passage of an introduced catheter.

FIG. 5 illustrates a cup-type articulating valve generally designated by reference number 56. Valve 56 is another articulating type valve which can be used as a replacement for leaflet valve assembly 24 shown in FIG. 1. For this embodiment, a valve passageway 58 is formed which has a generally conically shaped exit nipple 60. A cup shaped closure valve 62 is provided which is supported in cantilever fashion by arm 64 which normally biases the cup closure valve into sealing engagement with exit nipple 60, as shown in FIG. 6. FIG. 7 illustrates valve 56 when external catheter 32, reinforced with obturator 46 is initially penetrating valve passageway 58. During this process, external catheter 32 pushes cup closure valve 62 out of sealing engagement with valve nipple 60. FIG. 8 illustrates the orientation of the elements of cup closure valve 56 once external catheter 32 is fully introduced into the access port.

Figure 9:
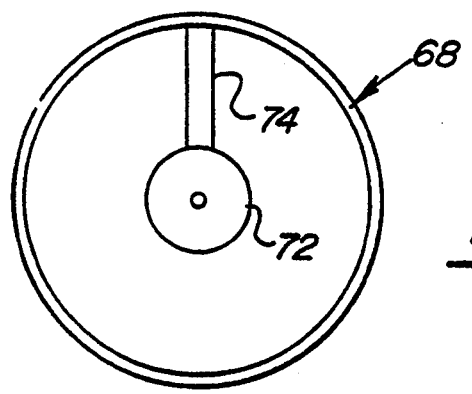
FIG. 9 is a frontal view of a catheter valve of the ball-and-seat variety which is an alternate embodiment of an articulating type valve.
Figure 10:
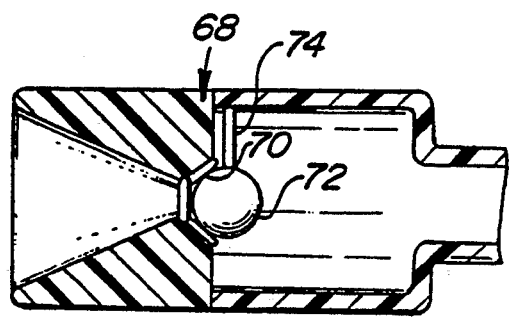
FIG. 10 is a cross-sectional view from FIG. 9 showing the ball valve in a fully closed condition.
Figure 11:
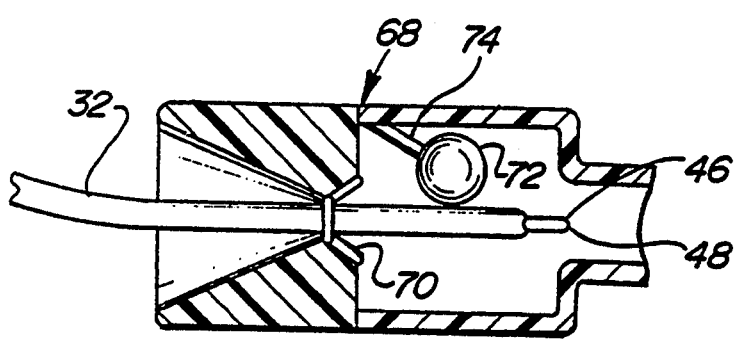
FIG. 11 is a cross-sectional view taken from FIG. 9 showing the ball valve in a fully opened condition.

FIG. 9 illustrates another embodiment for an articulating valve in the form of a ball-and-seal valve, generally designated by reference number 68. Ball-and-seat valve 68 defines a conical ball seat 70 with ball closure valve 72 which is normally biased into sealing engagement with the ball seat by arm 74. Operation of ball-and-seat valve 68 is similar to the operation of cup valve 56 previously described. In both cases, external catheter 32 (or another filament), which may be stiffened by an obturator 46, physically unseats the valve element to permit passage of the external catheter.

Although the leaflet, cup, and ball-in-socket catheter valves described previously differ in their construction, each can be described as an "articulating" valve in that the introduced filament is accurately guided into an insertion area for the valve and deflects an element to the valve in a predictable and repeatable manner to permit passage of a catheter or other filament. These valve types are further distinguishable over the previously used septums in that they are not randomly punctured and physically damaged with each insertion of the filament. It is submitted that there are numerous additional articulating, non-destructive valve designs which achieve the desired characteristics and which could be utilized in the embodiments of the present invention. The application should therefore not be interpreted as being limited to the specific embodiments disclosed herein.

Figure 12:
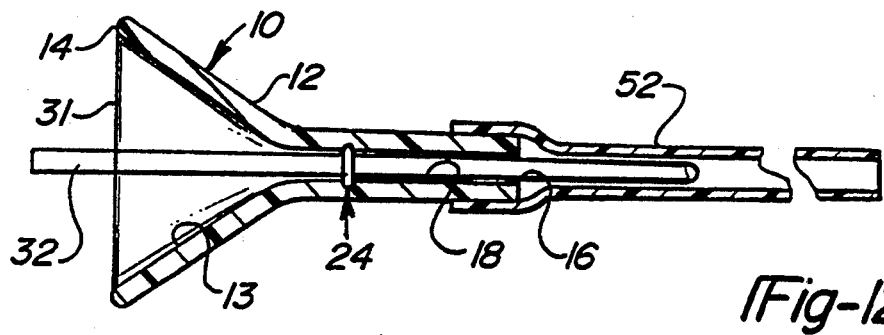
FIG. 12 is a cross-sectional of an embodiment of this invention similar to FIG. 1, illustrating that an external introduced catheter may be placed well into the internal catheter of the access port.
Figure 13:
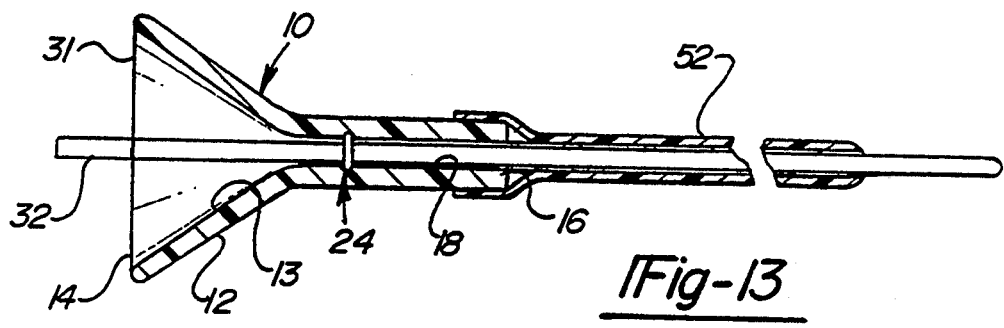
FIG. 13 is a cross-sectional view similar to FIG. 12 except showing the introduced catheter being fed through the access port such that its terminal end is beyond the terminal end of the internal catheter.

FIG. 12 illustrates access port 10 described previously and shows that once external catheter 32 penetrates leaflet valve assembly 24 (or any other type of articulating valve used), the external catheter can be positioned at any desired point along internal catheter 52. FIG. 13 is a view similar to FIG. 12 but shows that external catheter 32 can be fed through access port 10 so that its terminal end extends beyond that of internal catheter 52. This feature allows access port 10 to be readily adapted for angiography and angioplasty procedures.

Figure 14:
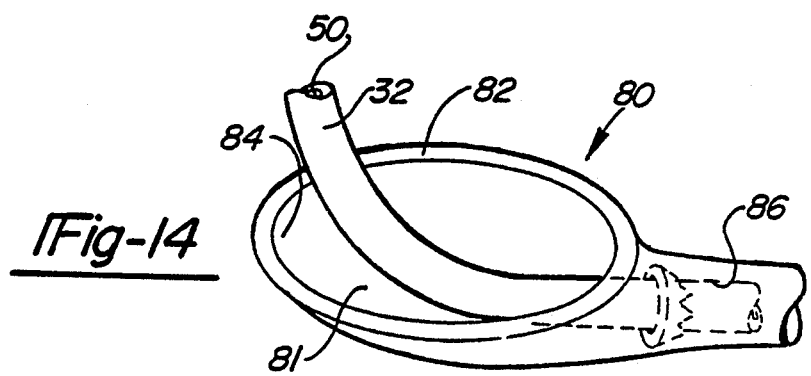
FIG. 14 is a pictorial view of an access port in accordance with a second embodiment of this invention shown providing a change in angle for the external introduced catheter.
Figure 15:
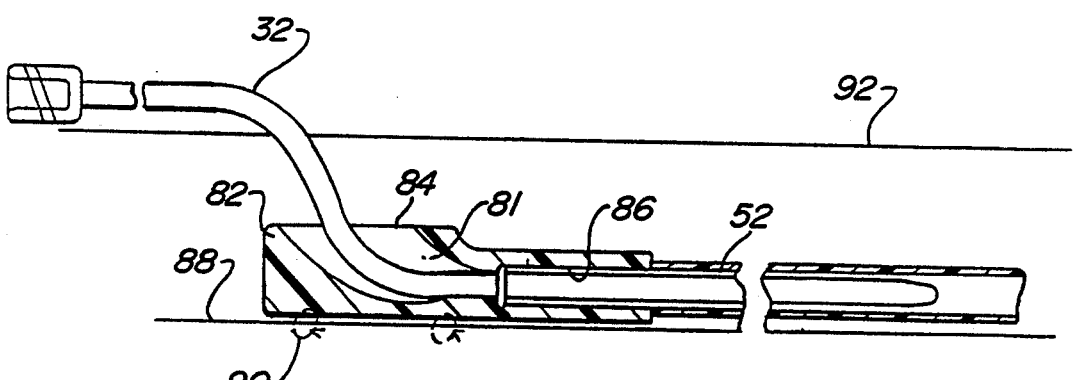
FIG. 15 is a cross-sectional view taken from the access port of FIG. 14 showing the access port in use and showing an externally introduced catheter in position for access with the patient.

Now with reference to FIGS. 14 and 15, a second embodiment of an access port according to this invention is shown which is generally designated by reference number 80. Access port 80 differs principally from access port 10 in that the internal cavity 81 of housing 82 is in the shape of a curved, bent or twisted funnel or horn such that a line normal to the plane defined by entrance orifice 84 is generally at a right angle to the longitudinal central axis of exit passageway 86. Like the first embodiment, access port 80 employs an articulating valve, such as a leaflet valve assembly 24 as previously described.

Access port 80 has a smooth inside surface 81 which is shaped to have a decreasing cross sectional area from the perimeter of entrance orifice 84 to exit passageway 86 for guiding external catheter 32 into registry with the exit passageway. The configuration of access port 80 is desirable where a large target area is needed which is generally parallel to the surface of the patient's skin overlying the device. In all other respects, access port 60 is constructed and used in the manner consistent with that of access port 10 previously described. FIG. 15 provides an illustration of access port 80 in use for infusing a patient. Port 80 is shown fastened to support tissue 88 by sutures 90 below skin 92 of the patient. As in the prior embodiments, the port could be subcutaneously mounted by methods not requiring or using fasteners.

Figure 16:
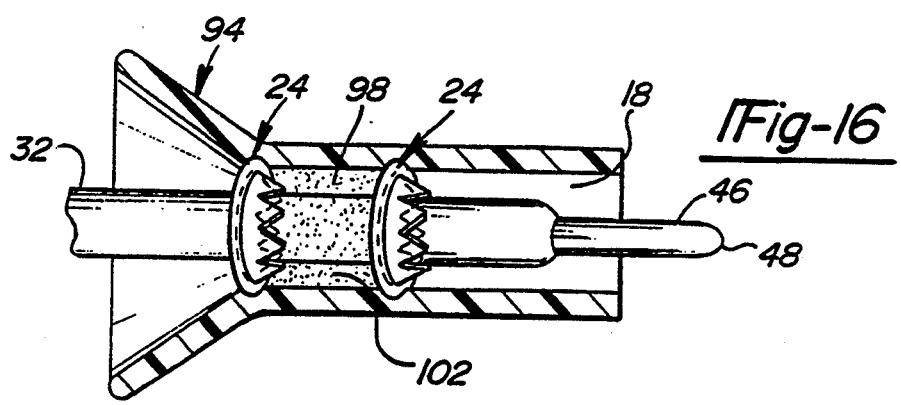
FIG. 16 is a partial cross-sectional view of an access port in accordance with a third embodiment of this invention shown employing a pair of separated leaflet valves which provide a reservoir for an antimicrobial fluid which provides enhanced resistance against infection.

FIG. 16 is a partial sectional view of an access port 94 according to a third embodiment of this invention. This embodiment differs from those described previously in that a pair of leaflet valve assemblies 24 is provided along internal passageway 18 to define an enclosed internal cavity 98. Internal reservoir or cavity 98 is provided so that an antimicrobial solution 102 can be retained as a means of inhibiting the introduction of infectious agents into the patient through the process of infusion.

Figure 17:
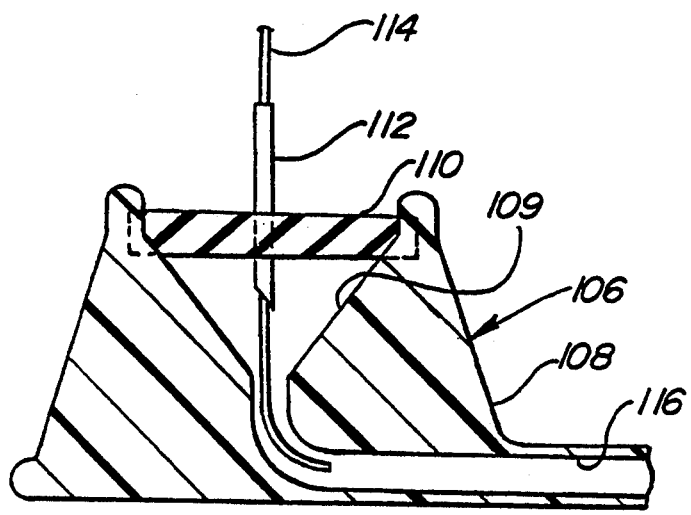
FIG. 17 is a cross-sectional view of an access port in accordance with a fourth embodiment of this invention employing a conventional rubber septum but having means for guiding a catheter or guide wire through a bend and into or beyond the port exit orifice.

FIG. 17 illustrates an access port in accordance with a fourth embodiment of this invention which is designated by reference number 106. Like the second embodiment shown in FIG. 14, access port housing 108 has an internal cavity 109 which causes an external catheter or other filament to undergo a right angle bend as it is fed into the device. However, access port 106 does not incorporate an articulating valve, but rather uses the conventional approach of using a compressed rubber septum 110. In use of this embodiment, a hypodermic needle 112 penetrates septum 110 and a small diameter catheter 114 is fed through needle 112. As discussed previously in connection with FIG. 14, the internal surface configuration of housing cavity 109 causes catheter 114 to be guided into and through passageway 116, and if desired, into the attached internal catheter (not shown). This embodiment also provides the advantages that a guide wire can be fed through needle 112 to clear thrombosis or other obstructions occurring within the device or in the attached internal catheter.

Figure 18:
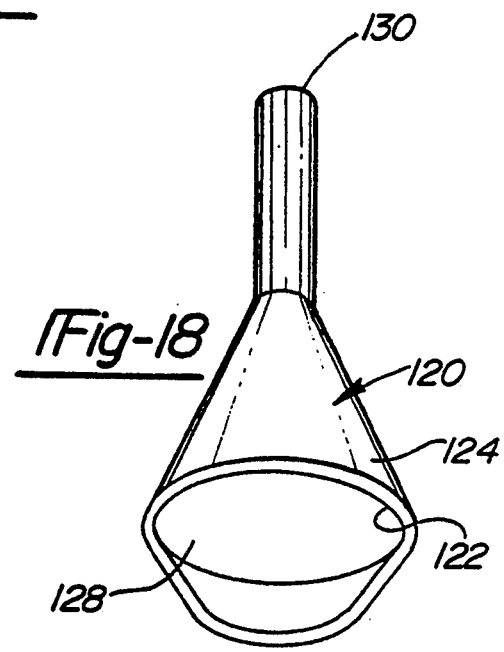
FIG. 18 is an access port in accordance with a fifth embodiment of this invention having an elliptically shaped entrance mouth.
Figure 19:
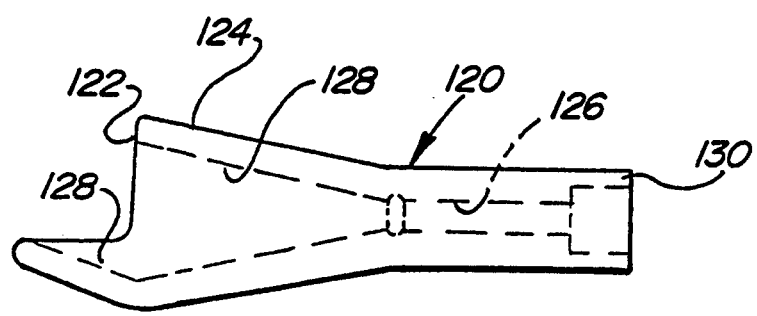
FIG. 19 is a side view of the access port shown in FIG. 18.

FIGS. 18 and 19 illustrate a fifth embodiment of an access port 120 according to this invention which may have an articulating valve as described previously, or may employ a compressed rubber septum like that of the embodiment shown in FIG. 17. These figures, however, illustrate that entrance opening 122 can form a generally elliptical configuration, as opposed to the previously seen circular configuration, such that the target area for the access port has an increased or greatest area when entering the device from a direction between alignment with the exit passageway 126, or at right angle to exit passageway. In other words, a line normal to entrance opening 122 forms an obtuse angle to the axis of exit passageway 126. Like the prior embodiments, housing 124 has a smooth internal surface which is shaped to include a guide lip 128 which aids in introducing an external catheter into passageway 126.

Figure 20:
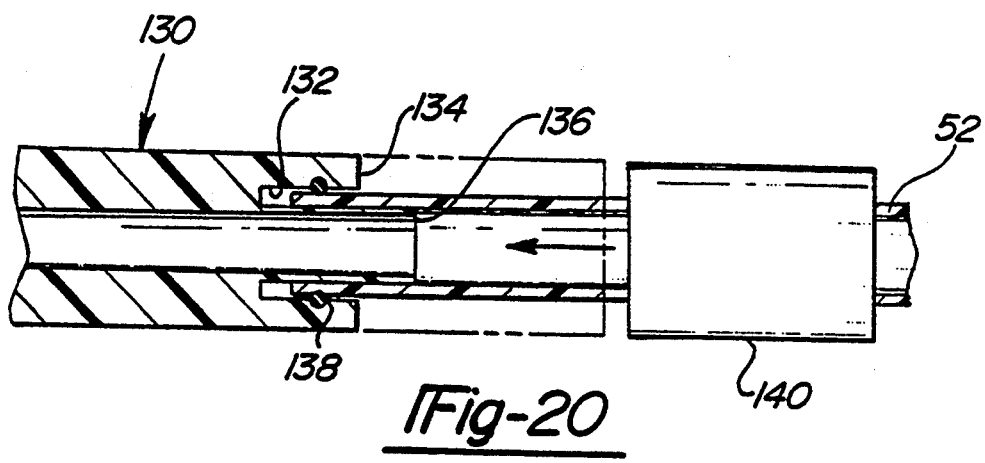
FIG. 20 is a cross-sectional view illustrating a manner of connecting an internal catheter to an access port in accordance with this invention, incorporating an annular chamber for receiving the internal catheter.

FIGS. 20 through 23 illustrate various means for attaching an internal catheter 52 to an access port. For the embodiment of FIG. 20, the access port features an exit end 130 defining an annular gap 132 formed between an outer tubular portion 134 of the exit outlet 134 and an inner tubular portion 136. Internal catheter 52 is slid onto inner tube 136 and into annular gap 132. Sealing means such as a gasket or 0-ring 138 can be provided to enhance the integrating of the fluid tight connection. Compression ring 140 can be used which is slid onto the connection as shown in FIG. 20 to exert a compressive force on internal catheter 52, further securing it to the access port. Compression ring 140 also acts as a stress reliever to prevent kinking of the internal catheter 52 at its connection point to the access port.

Figure 21:
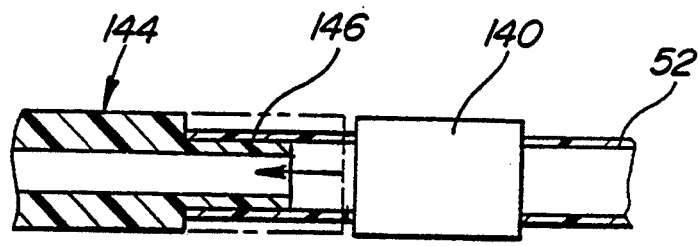
FIG. 21 is a cross-sectional view of another means of attaching an internal catheter to an access port according to this invention, in which the catheter is placed over a smooth cylindrical surface and a compression ring is slid onto the junction.

FIG. 21 illustrates another means for connecting internal catheter 52 to an access port. In this embodiment, exit end 144 has a reduced diameter projecting nipple 146 which internal catheter 152 is slid over. Like the embodiment shown in FIG. 20, compression ring 140 is provided which is slid onto the connection with FIG. 20.

Figure 22:
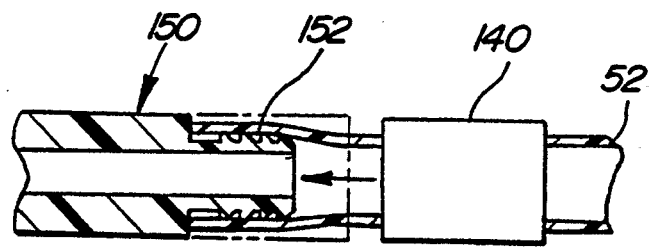
FIG. 22 is a cross-sectional view of still another approach toward connecting an internal catheter to an access port incorporating a barbed nipple on the access port and a compression ring.

FIG. 22 illustrates an access port exit end 150 which features reversibly oriented barbs 152 which serve to securely engage the inner surface of internal catheter 52. Again, compression ring 140 is used to enhance the security of the connection of the internal catheter to exit end 150.

Figure 23:
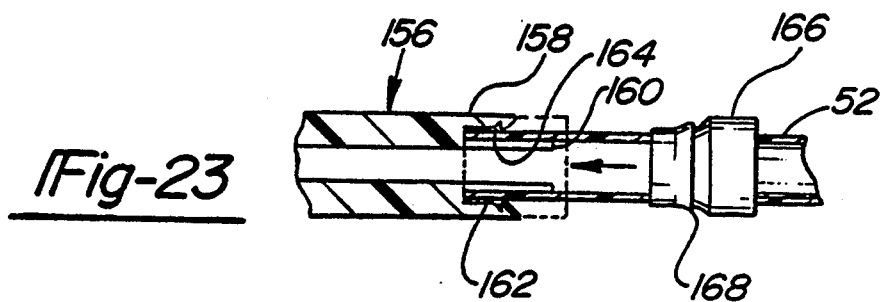
FIG. 23 is another means for attaching an internal catheter to an access port according to this invention incorporating an interlocking compression ring.

FIG. 23 illustrates still another approach toward connecting internal catheter 52 to an access port exit end 156. This embodiment, like that shown in FIG. 20, defines an outer tubular portion 158, an inner tubular portion 160, with annular gap 162 therebetween. For this embodiment, however, the inside diameter surface of outer tubular portion 158 defines groove 164. Compression ring 166 has an exterior configuration including annular barb 168 which interlocks with groove 164 when the compression ring is slid onto exit end 156.

Figure 24:
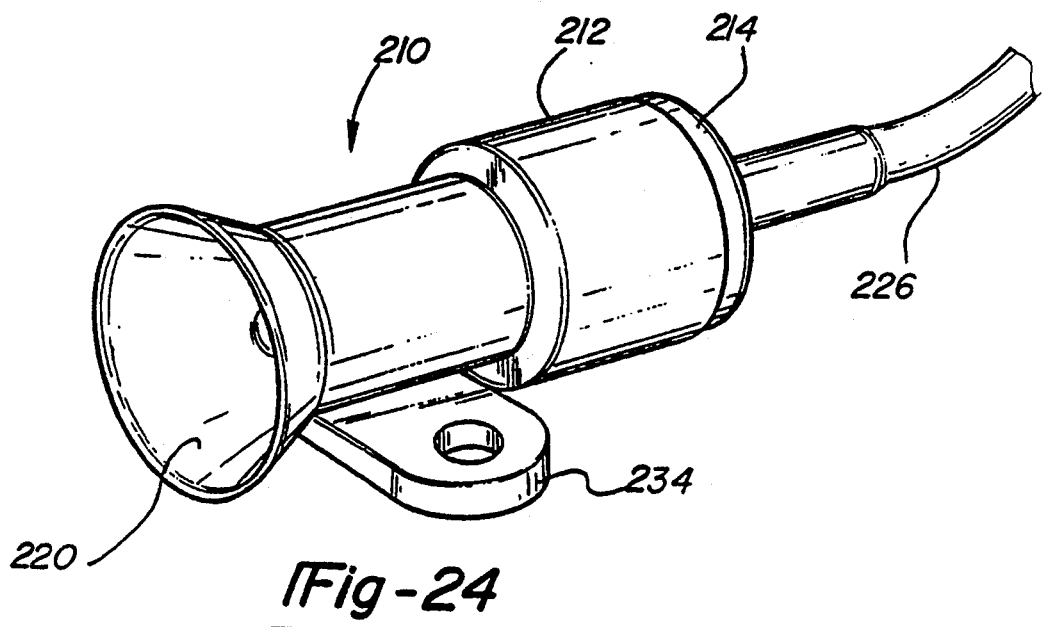
FIG. 24 is a pictorial view of an access port in accordance with a sixth embodiment of this invention shown attached to an internal catheter.

An access port in accordance with a sixth embodiment of this invention is shown in FIG. 24 and is generally designated there by reference number 210. Access port 210 principally comprises housing 212, outlet plug 214, and articulating valve assembly 216.

Figure 27:
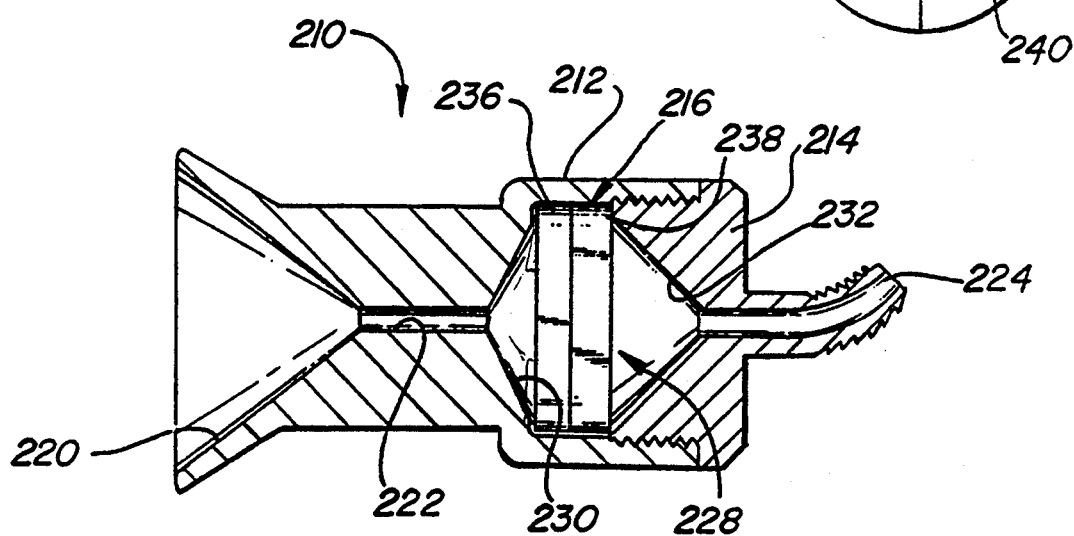
FIG. 27 is a cross-sectional view taken from FIG. 24 showing the internal construction of the access port according to this invention.

As best shown in FIGS. 24 and 27, housing 212 defines a funnel-shaped entrance orifice 220, the function of which is to guide an access needle 218 toward its center. Although orifice 220 is shown in the shape of a circular cone, other configurations could be used such as elliptical or flattened cones could be used to define the orifice opening. Such alternative shapes could be used to decrease the profile height of the device. Any configurations used for orifice 220 must posses a decreasing cross-sectional area for the purpose of guiding the access needle to a focus point. At the base of the orifice cavity shown in FIG. 27 is a reduced diameter guide passageway 222. Guide passageway 222 is straight and has a diameter only slightly greater than a diameter of elements which are desired to be passed into port 210.

Figure 25:
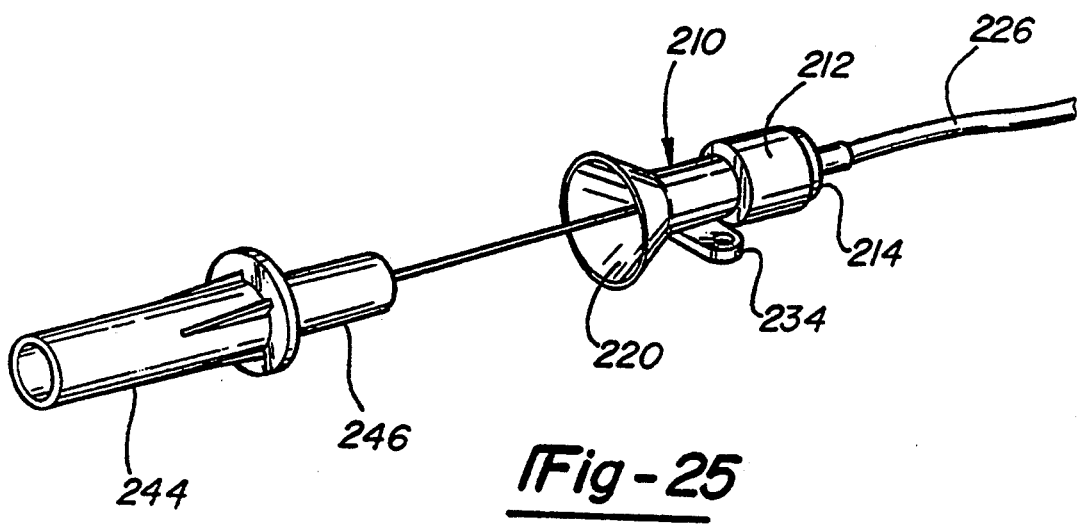
FIG. 25 illustrates an access needle with an external catheter being used to penetrate the access port shown in FIG. 24.
Figure 26:
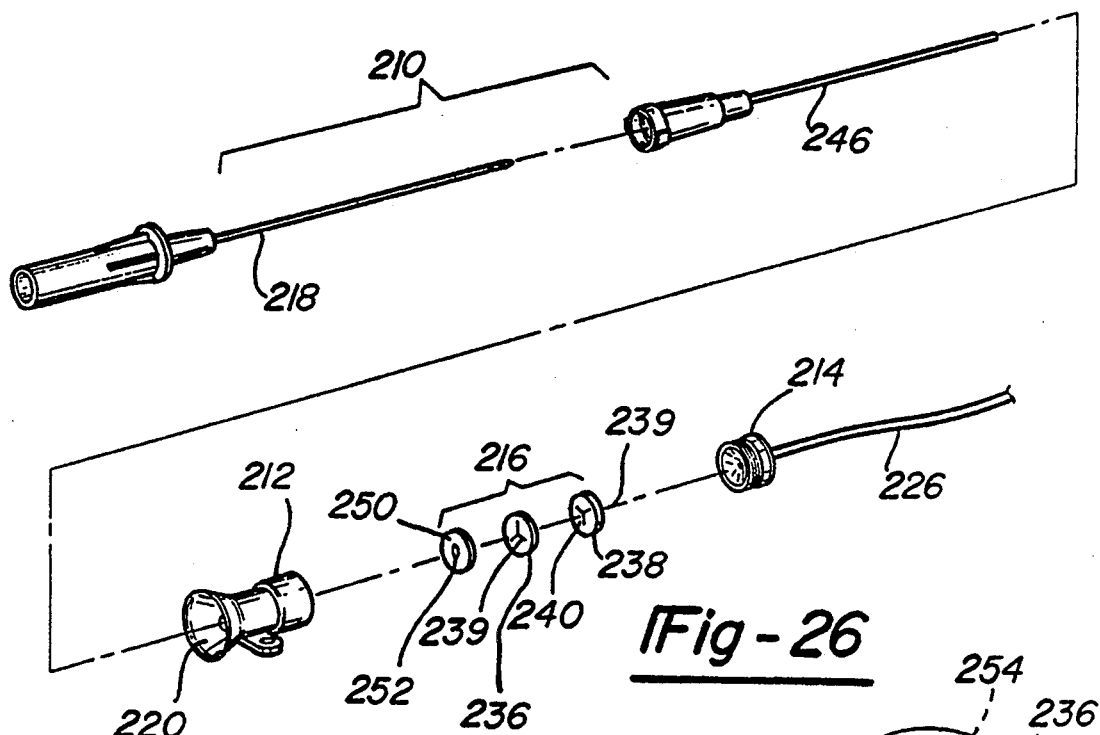
FIG. 26 is an exploded pictorial view of the access port of this invention illustrated in FIG. 25 shown with an optional elastic ring sealing disc for use with the leaflet valve elements.

Outlet plug 214 is externally threaded which enables it to be attached to the end of housing 212 opposite entrance orifice 220. Outlet plug 214 defines an externally barbed projecting hollow post 224 which enables an internal catheter 226 to be slid onto the post and attached to the access port as shown in FIGS. 24, 25 and 26. Hollow post 224 can be intentionally bent as shown in FIG. 27 to prevent needle 218 from passing entirely through the device in which case it could damage internal catheter 226. As is best shown in FIG. 27, once assembled together, housing 212 and outlet plug 214 define an internal cavity 228 which accommodates leaflet valve assembly 216. As shown in FIG. 27, cavity 228 is in an area of increase volume defined by a pair of conical surfaces 230 and 232, with conical surface 230 joining with guide passageway 222 and conical surface 232 joining with exit plug post 224.

Mounting plate 234 is attached or formed integrally with housing 212 and provides a means of mounting access port 210 to support tissues within a patient either with or without using sutures, surgical staples, etc.

Leaflet valve assembly 216 shown in FIG. 27 includes a pair of elastic leaflet valve discs 236 and 238. Each of the elastic discs include slits extending from their geometric center and radially outward toward the perimeter of the elastic disc to define three separate flaps or leaves 240. Elastic discs 236 and 238 are stacked against one another in a manner to disalign cuts 239 so that the leaves 240 of each disc overlies the cuts in the other to enhance the sealing characteristic of the leaflet valve assembly. As shown in FIG. 27, when housing 212 and outlet plug 214 are assembled together, the outer periphery of elastic discs 236 and 238 are slightly compressed to provide a seal which prevents fluids from leaking around the outer edges of the elastic disc elements.

FIG. 26 shows an optional disc ring valve element 250 (not shown in FIG. 27) which is provided to further enhance the sealing characteristics of valve assembly 216. Disc element 250 is donut shaped and has a hole 252 through its center, which has a diameter slightly smaller than the needle or catheter which port 210 is designed to accommodate. The inventors have found that a valve element 250 having a durometer hardness of 50 Shore A and a thickness of 0.040 inches operates with the desired characteristics in the present invention. Valve element 250 is positioned to be the first element encountered by the access needle. This orientation is provided to prevent the apexes of leaves 240 from damaging valve disc 250 or interfering with its sealing capability.

Access port 210 in accordance with this invention is adapted to be accessed using a conventional hypodermic needle 218 or trocar with a sharp end, which can be hollow or solid depending on the intended application. Needle 218 can be used by itself or with an external catheter 246, which the needle is slid through so that the needle and catheter combination (eg. the commercially available "ANGIOGATH" ™, product) can be pierced through the skin and positioned into port 210 allowing the needle to be later withdrawn, leaving catheter 246 inside port 210 to provide fluid flow into or from the patient. The introduced catheter 246 can be threaded into internal catheter 226 to any extent desired, preventing unintentional withdrawal of the introduced catheter.

FIG. 25 shows access port 210 being accessed by a needle 18 and catheter 246 combination. When the care provider desires to access port 210, needle 218 is used to pierce the patient's skin at an area adjacent the port entrance orifice 220 and the needle is pushed into the port. Entrance orifice 220 receives the sharp end of needle 218 and guides it toward and into guide passageway 222. The guide passageway then orients needle 218 and aims it to strike leaflet valve assembly 216 at the center of valve elements 236 and 238, which is the point of intersection of the cuts 239 defining leaves or flaps 240. Guide passageway 222, therefore, guides needle 218 to strike leaflet valve assembly 216 in an area where cutting or damage to the elastic disc elements is minimized since the discs are most easily penetrated at their central region where their flexibility is greatest.

Figure 28:
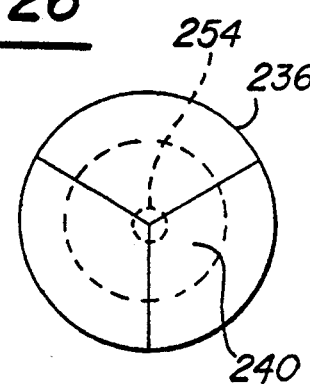
FIG. 28 is a frontal view of the elastic leaflet valve elements as shown in FIGS. 26 and 27.

In order to provide an acceptable resistance to damage of valve assembly 216 by needle 218, it is believed that the diameter of passageway 222 which is superimposed on disc 236 in FIG. 28 and designated by reference number 254, should be no larger than one-half the diameter of the slit portion of elastic discs 236 and 238 which is encompassed by a circle designated as diameter 256. Passageway diameters 254 greater than that ratio would permit an inserted needle with its sharp point to strike the leaflet valve assembly 216 at near its outer perimeter, where leaves 240 are not as supple and are more likely to be pierced by the access needle than the center portion. Controlling the position of the inserted needle 218 also protects elastic disc 250 from damage which would occur if the needle struck outside of hole 252.

The conical surfaces 230 and 232 of valve cavity 228 are provided to accommodate the flexing of valve leaves 240 in both directions. When access needle 218 is inserted into access port 210, the leaves 240 are permitted to deflect toward hollow post 224. In addition, conical cavity 232 insures that the access needle 218 or other introduced filament is properly guided to pass through hollow post 224 and into internal catheter 226, if desired. Upon withdrawal of access needle 218 or catheter 246 from access port 210, conical surface 230 enables the leaves 240 of valve assembly 216 to be freely deflected in an opposite direction.

During the step of inserting needle 218 into port 210, a positive indication of full insertion is felt by the attending care provider as needle 218, which is relatively rigid, engages the bent portion of hollow post 224. This stop is provided to prevent accidental damage to internal catheter 226. However, the introduced filament or catheter 246 which is more flexible than access needle 218 can be readily threaded past hollow post 224 to provide deep insertion.

In addition to permitting the insertion of a needle 218 and catheter 246 to port 210, this invention would allow a guide wire to be introduced into the port through access needle 218 which could be fed through the device and into and through the internal catheter 246 to remove thrombosis or other clogging problems. Various other filaments type elements could also be used with port 210 such as optical fibers, electrical conductors, remote sensing systems, etc.

Numerous materials may be used to form housing 212. Since housing 212 will be subject to being struck by sharp needles which must be redirected into guide passageway 222, it is desirable to form the housing or at least the surface of entrance orifice 220 of a hard material such as stainless steel or titanium or a hard ceramic. Soft materials such as plastics, if used to form the inside surface of entrance orifice 220 could be subject to being gouged by needle 218, preventing proper guiding of the access needle. Similarly, exit outlet plug 214 is subject to being struck by a sharp needle and should also be made of a hard metal material for the reasons mentioned in connection with housing 212. Elastic discs 236, 238 and 250 can be made of numerous elastic materials such as silicone rubber.

Figure 29:
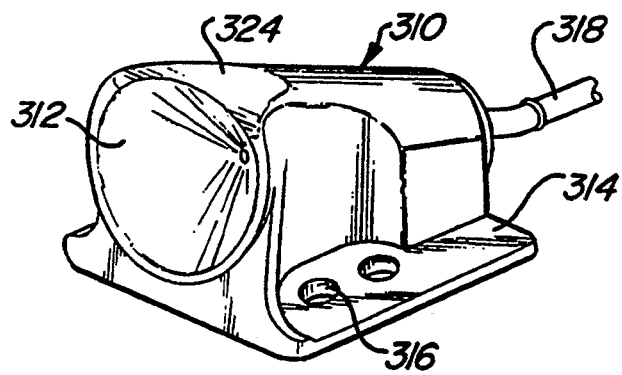
FIG. 29 is a pictorial view of an angled access port according to a seventh embodiment of this invention.
Figure 30:
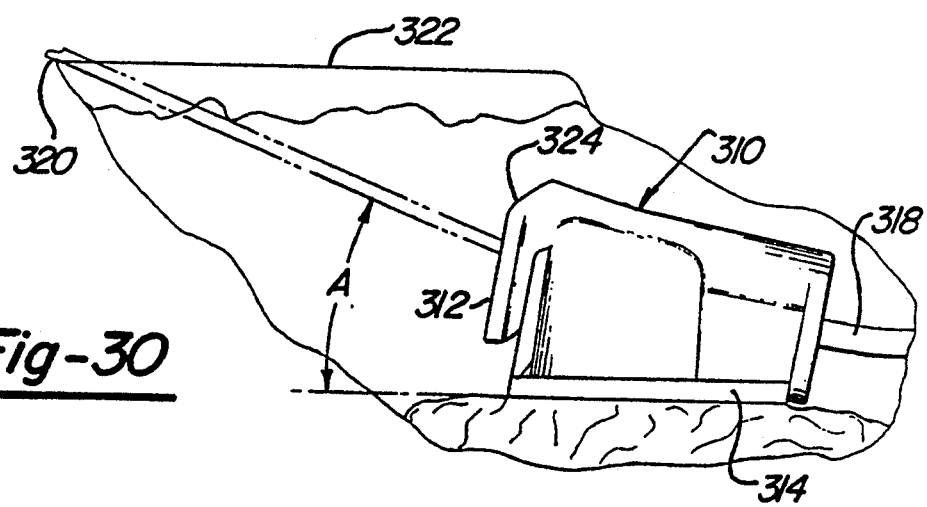
FIG. 30 is a side view of the port shown in FIG. 29 shown implanted within a patient and being accessed by a penetrating needle which introduces a flexible external filament.

An access port in accordance with a seventh embodiment of this invention is shown in FIGS. 29 and 30 and is generally designated by reference number 310. Port 310 is designed to be accessed using a sharp needle which passes into the port through funnel shaped entrance orifice 312. Port 310 also includes a mounting pad 314 defining a generally planer mounting surface and may include apertures 316 for sutures or staples further enabling the device to be secured to appropriate support tissue within the patient. Internal catheters 318 is shown attached to port 310 and is tunneled to a desired site within the patient.

The embodiment shown in FIGS. 29 and 30 of this invention is presented to disclose two specific improvements to devices described previously, namely a modified entrance orifice 312 and an inclination of the device with respect to mounting pad 314. As best shown in FIG. 30, access port 310 is oriented such that the accessing needle 320 (and associated catheter or other introduced filament) shown in phantom lines enters the device at an angle, designated as angle A from a plane parallel to mounting pad 314. The inclined orientation of port 310 facilitates insertion of needle 320 through the patient's skin 322, as shown in FIG. 30.

The further improvement shown in FIGS. 29 and 30 for access port 310 involves a removal of the upper surface of the housing in the area defining entrance orifice 312 shown as a recessed or scalloped region 324. Removing material and forming the discontinuity in the scalloped region 324 has the effect of slightly enlarging the target area of entrance orifice 312, and also providing a more smooth surface which is covered by the patient's skin, thus making the device somewhat less conspicuous to the patient and possibly less irritating.

Although the features of access port 310 discussed in conjunction with FIGS. 29 and 30 are employed in a port of the type shown in FIG. 24, these improvements could also be incorporated into ports having various constructions and internal features including other ports which are described in this application and disclosed in the related applications.

Figure 31:
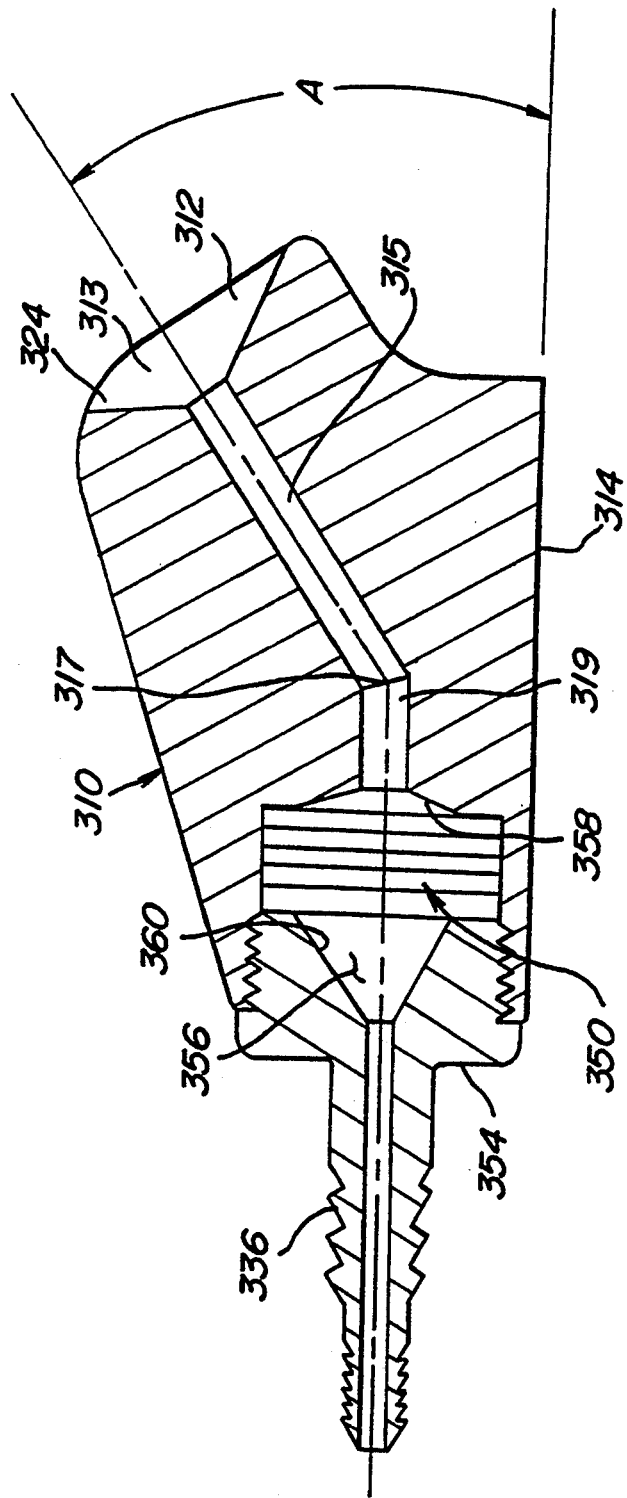
FIG. 31 is a cross-sectional view of the access port shown in FIGS. 29 and 30.

Referring now to FIG. 31, where access port 310 is shown in cross-section, entrance orifice 312 is in the form of a conical surface 313, which forms the outer perimeter of the orifice 312, that defines a relatively shallow cone having a relatively large included cone angle. Conical surface 313 joins with a smaller constant diameter passageway 315 which is provided as a means of guiding inserted needle 320 toward an apex or focus area 317 of orifice 312. The focus area 317 joins with entrance passageway 319 which leads to an articulating valve assembly 350. The valve assembly 350 is only being briefly described in connection with FIG. 31 since it is described in greater detail with respect to the embodiment shown in FIG. 33 through 40.

For reasons which will be better described later in this specification, passageway 317 is intentionally oriented at a relatively great off-axis angle with respect to the central generating axis of entrance orifice 312. This off-axis orientation provides a curved passageway which is intended to prevent an introduced rigid needle 320 from undergoing the turn and directly engaging articulating catheter valve assembly 350. This feature accordingly distinguishes access port 310, and access port 330 which is further discussed hereafter, from the embodiments described previously which are designed to enable an inserted needle or rigid introducer to pass directly through an articulating valve.

Figure 32:
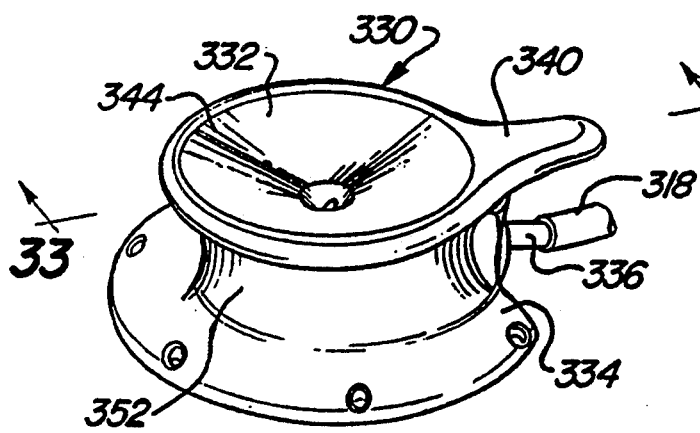
FIG. 32 is a pictorial view of an eighth embodiment of an access port according to this invention.

FIG. 32 illustrates access port 330 in accordance with an eighth embodiment of this invention. Access port 330 is primarily intended to be implanted in the chest wall region of a patient and generally comprises a funnel shaped entrance orifice 332, mounting platform 334, outlet tube 336, and a valving system which is described below.

Mounting platform 334 can feature apertures 338 for enabling port 330 to be secured to underlying tissue within a patient using sutures, staples, etc.

Figure 33:
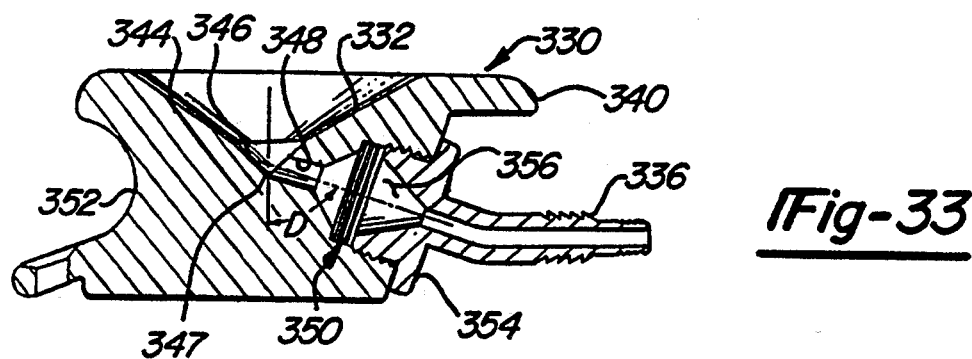
FIG. 33 is a cross-sectional view taken along line 33—33 from FIG. 32.

As best shown in FIG. 33, access port housing 352 also features a radially projecting protuberance in the form of a lug or ledge 340 projecting away from entrance orifice 332, and overlying outlet tube 336. By providing such an irregular feature on the device housing 352, the orientation of the port, and in particular, outlet tube 336 and internal catheter 318 can be readily ascertained through palpation of the device by the clinician. As will be better described in the following paragraphs, for some embodiments it is necessary to cause the introduced filament to undergo a rather sharp turn upon entrance into the device, and, therefore, knowing the orientation of the port can aid in feeding in the introduced filament. Lug 340 also provides the additional benefit of shielding implanted catheter 318 from needle sticks by the accessing hypodermic needle 320, if improperly aimed.

Figure 35:
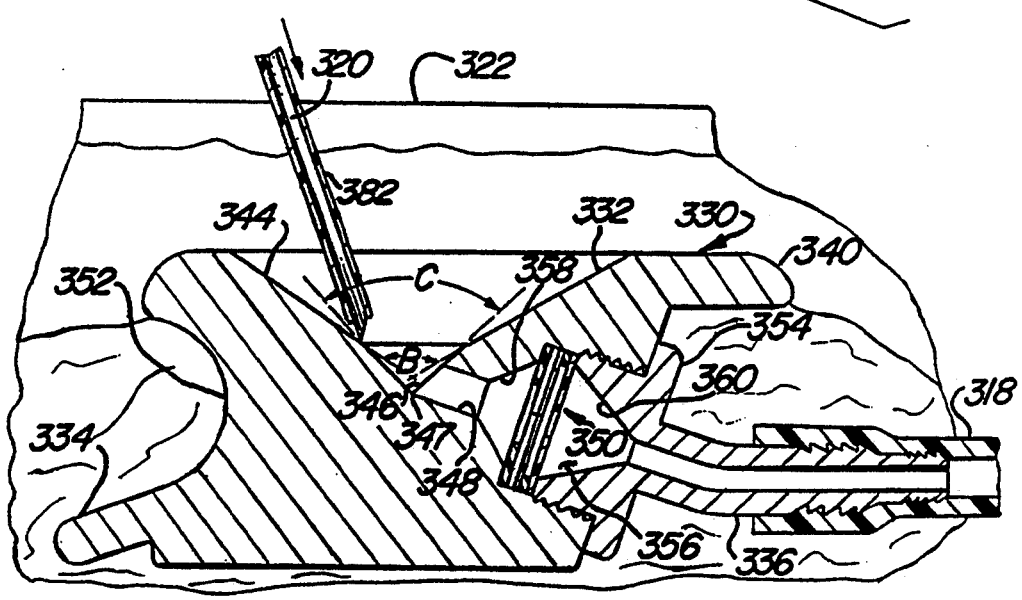
FIG. 35 is an enlarged cross-sectional view similar to FIG. 33 but showing an accessing needle being introduced into the port.

Now with the reference to FIGS. 33 and 35, the configuration of entrance orifice 332 can be described in more detail. As is apparent from the figures, entrance orifice 332 is in the from of a pair of joined conical surfaces having differing cone angles. The first conical surface 344 which forms the outer perimeter of the orifice defines a relatively shallow cone having a relatively large included cone angle identified as angle B in FIG. 35. Conical surface 344 joins with a smaller diameter conical surface 346 having an included angle, identified as angle C in the figure, which is smaller than angle B. The shallower conical surface 344 is provided as a means of guiding inserted needle 320 toward the apex or focus area 347 of orifice 312. The relatively large angle B of conical surface 344 is provided so that the distance through access port 330 between its top planer surface and the internal valve system is kept as small as reasonably possible while providing a large target area for needle 320. This total distance is significant in that presently employed catheters which are fed over needles (eg. "ANGIOCATH") have a relatively short length, i.e. approximately two inches. It is desirable to allow such existing needles and catheters to be used with port 330, and at the same time, insure that the introduced catheter is securely inserted into the access port and engaged with the internal valve. Conical surface 346 is provided with a smaller included angle as a means of securely engaging introduced needle 330 and restraining it from radial motion once it is inserted and becomes rested in focus area 347.

While the benefits of the configuration of entrance orifice 312 are achieved in accordance with the illustrated embodiment using two joined conical segments, it is fully within the scope of this invention to provide an entrance orifice defined by various other surfaces having a progressively decreasing cone angle as measured as shown in FIG. 35 when moving from the outer perimeter of entrance orifice 332 to the focus area 347. For example, a paraboloid surface could also be provided for orifice 332. In addition, entrance orifice 332 could be defined by a surface which is a asymmetrical in the sense of not being a surface of revolution about an axis through the orifice. Many surfaces can be imagined providing the benefits of the invention through providing a progressively smaller cone angle or target surface as the focus area is approached.

As is shown in FIG. 35 the relatively large angle of conical surface 344 serves to provide a low height between the upper surface of access port 330 and articulating valve 350. As mentioned previously, this is advantageous since standard introduced catheters have a relatively short length and it is desirable to make sure they are fully engaged with the articulating valve to preclude inadvertent withdrawal.

The focus area 347 of entrance orifice 332 joins with entrance passageway 348 which leads to an articulating valve assembly 350. Passageway 348 is intentionally oriented with respect to the central generating axis of entrance orifice 332 at a relatively great off-axis angle, shown as angle D in FIG. 32 of about 60 degrees. As with the embodiment of FIG. 31, this off-axis orientation provides a curved passageway which is intended to prevent an introduced rigid needle 320 from undergoing the turn and directly engaging articulating valve assembly 350. Again, this feature accordingly distinguishes access port 330 from the embodiments described previously which are designed to enable a rigid introducer or needle to pass directly through the articulating valve. The feature, however, can be readily adapted and used with the previous embodiments.

Housing 352 is preferably made from a hard material, such as a metal, which will not be gouged or engaged by the accessing needle 320. For example, titanium or another hard metal could be used to form the entrance housing 352, or could be used merely to form the surface of entrance orifice 332.

As best shown in FIGS. 33 and 35, access port housing 352 and outlet plug 354 define catheter valve cavity 356. As shown in these figures, cavity 356 is bounded by a pair of conical surfaces including conical surface 358 which joins with passageway 348, and conical surface 360 formed by outlet plug 354. The included angle defined by conical surface 358 is greater than that of conical surface 360. The conical surfaces 358 and 360 are provided to enable flexing of the elements comprising articulating valve 350.

Figure 34:
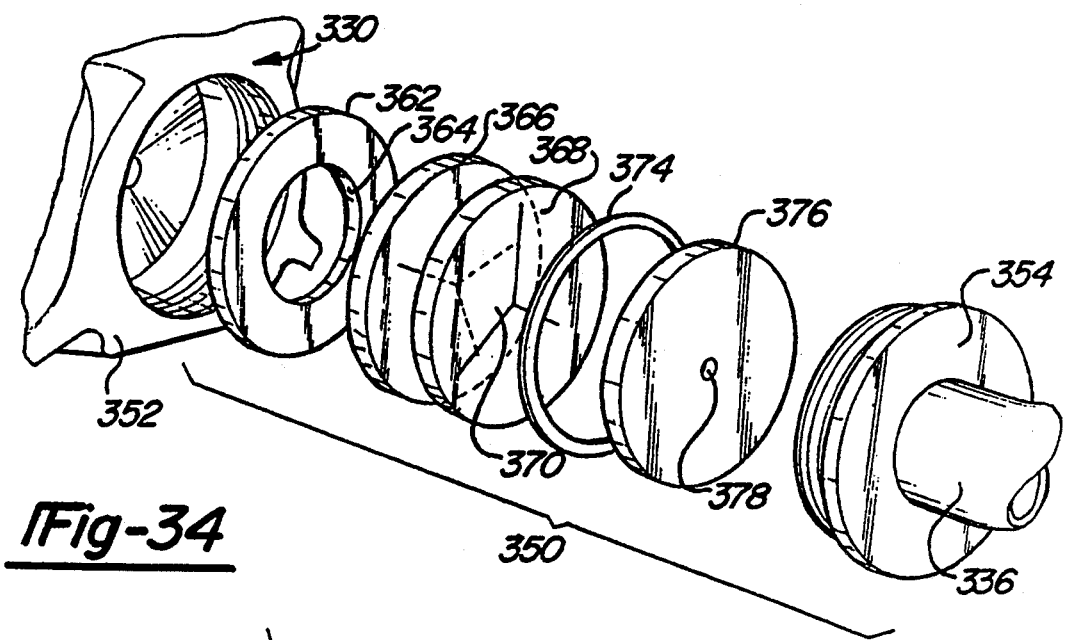
FIG. 34 is an exploded pictorial view of the valve of the port shown in FIGS. 32 and 33.

FIG. 33 provides an exploded view of articulating valve assembly 350. The valve is comprised of a number of individual valve elements stacked together. The first valve element encountered when passing through valve 350 from entrance orifice 332, is a ring or donut valve 362, which is comprised of a ring of elastomeric material with a central circular aperture 364. Access port 330 can be used with introduced catheters of various diameters. Ring valve 362 is not provided to seal directly against the outer periphery of all sizes of introduced catheters, but rather provides a reinforcing function for the remaining catheter valve elements and also services to orient and center the introduced catheter, as will be described in more detail below. The next two valve elements are leaflet valve discs 366 and 368. Valve discs 366 and 368 each define three or more leaves 370 which form an apex at the geometric center of each valve disc. As shown in FIG. 34, the leaves of each valve disc 366 and 368 are intentionally disaligned or indexed to an offset position so that the leaves are not directly overlapping. This indexing is provided to enhance the sealing capabilities of catheter valve 350. The next elements encountered in valve 350 are spacer ring 374 and finally another ring or donut valve 376 with central aperture 378. Aperture 378 has a diameter which is slightly smaller than any of the catheters which access port 330 is designed to be used with, thus providing a firm perimeter seal for the introduced catheters. The elements comprising valve 350 are stacked together, inserted into valve cavity 356 and retained there through the threaded engagement between housing 352 and outlet plug 354.

Since hollow post 336 of outlet plug 354 is not oriented parallel to the plane defining mounting pad 314, the hollow post is bent slightly as shown in FIG. 33 as a means of orientating implanted catheter 318 along the plane defining port mounting platform 334.

FIGS. 35 through 38 are provided to show access port 330 in use, and in particular, show the process of introducing an external catheter into the device. FIG. 35 shows access port 330 implanted with a patient below the surface of skin 322. In FIG. 35, a hypodermic needle 320 is shown penetrating skin 322. Needle 320 is placed through catheter 382 of conventional design (eg. "ANGIOCATH"). Needle 320 and catheter 382 are inserted through the skin and into entrance orifice 332. Conical surface 344 initially guides the needle into conical surface 346, and finally into nesting engagement in focus area 347. As stated previously, orifice 312 is made from a material which will not be gouged by needle 320, but rather will guide it into focus area 347.

FIG. 36 shows accessing needle 320 being fully inserted into focus area 347 and into passageway 348. Due to the inclination of passageway 348 from the entrance orifice, needle 320 cannot readily pass beyond the point shown in FIG. 36. Once this position is reached, the care provider has positive feedback that the elements are oriented properly since it is apparent that the needle cannot be readily inserted any further into access port 310.

Once the point of FIG. 36 is reached, the care provider can slide catheter 382 along needle 320 while holding the needle in position, thus forcing the tip of catheter 382 further into access port 330. FIG. 36 illustrates in phantom lines that external catheter 382 undergoes a bend as it is fed into engagement with valve 350. Catheter 382 does not necessarily become oriented precisely along the longitudinal axis of passageway 348 and, therefore, does not always initially engage articulating valve assembly 350 at its center. Ring valve element 362 serves to aid in centering introduced catheter 382 to properly orient itself with respect to the remaining valve elements. As introduced catheter 382 is forced further into engagement with the catheter 350, it passes through leaflet valve discs 366 and 368. As discussed in the previous embodiments, the leaves 370 can be readily opened by inserting the external catheter and the triangular shape of the leaves 370 serves to aid in centering the catheter. Finally, the introduced catheter passes through second ring valve element 376 having a relatively small aperture 378. Due to the centering functions provided by ring element 362 and the leaflet element 366 and 368, the introduced catheter becomes accurately aligned with and forced through aperture 378. Aperture 378 is sized to provide a perimeter seal around the introduced catheter 382. A fully inserted catheter is shown in FIG. 38.

The design of articulating valve 350 according to this embodiment provides a number of significant features. By providing spacing ring 374, deflection of leaflet valve leaves 370 in the direction of the insertion of catheter 382 is freely permitted. When the introduced catheter passes through the leaflet valves, leaves 370 are permitted to deflect as shown in FIGS. 37 and 38 without significant restriction caused by the presence of ring valve element 376. However, upon withdrawal of introduced catheter 382, reverse deflection of valve leaves 370 causes them to be reinforced by the close proximity of valve element 362, thus providing a relatively greater amount of friction during withdrawal versus insertion of catheter 382. This difference in insertion versus withdrawal friction is a desirable feature since it allows the catheter to be freely inserted into the port, yet firmly engages the inserted catheter to prevent inadvertent withdrawal of it during infusion.

The differing cone angles provided by catheter valve cavity conical surfaces 358 and 360 also provide several other functions. The relatively large angle of conical surface 358 is provided to place the passageway 348 in close proximity to catheter valve 350. This enhances the "targeting" function to ensure that catheter 382 strikes the valve 350 at or near its center where it can be easily deflected and is guided into a proper engagement with ring valve element 376. This large cone angle also serves to limit the degree of deflection of ring valve element 362, thus increasing withdrawal friction. The relatively small cone angle of conical surface 360 is provided to guide the introduced catheter smoothly into hollow post 380 and provides clearance to permit relatively unrestricted deflection of leaflet valves 366 and 368 and ring valve element 376.

Figure 39:
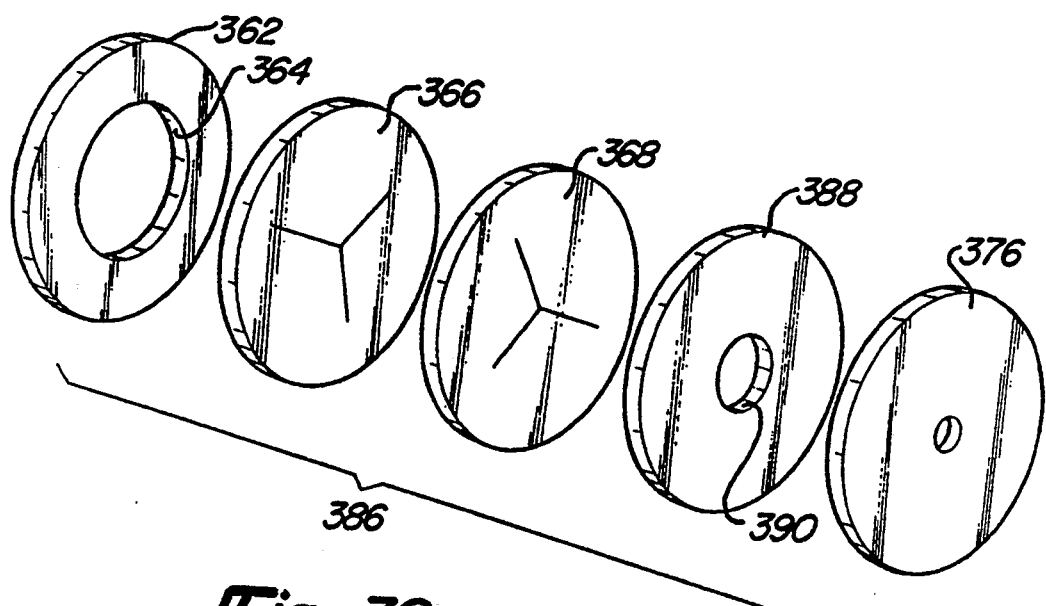
FIG. 39 is an exploded pictorial view of another embodiment of an articulating valve according to this invention.

FIG. 39 shows another embodiment of an articulating valve assembly and is designated by reference number 386. Valve assembly 386 has a number of elements identical to valve assembly 350 described immediately above, and the common elements are designated by common reference numbers. Valve assembly 386 differs from the previous embodiment in that spacer ring 374 is replaced with another donut or ring valve element 388, having an internal circular aperture 390. The function of ring valve element 388 is to reinforce leaves 370 of valve disc 368 as a means of enhancing the sealing capabilities of valve assembly 386. The diameter of aperture 390 is chosen to be larger than any introduced catheter 382 with which valve assembly 386 would be used.

Figure 40:
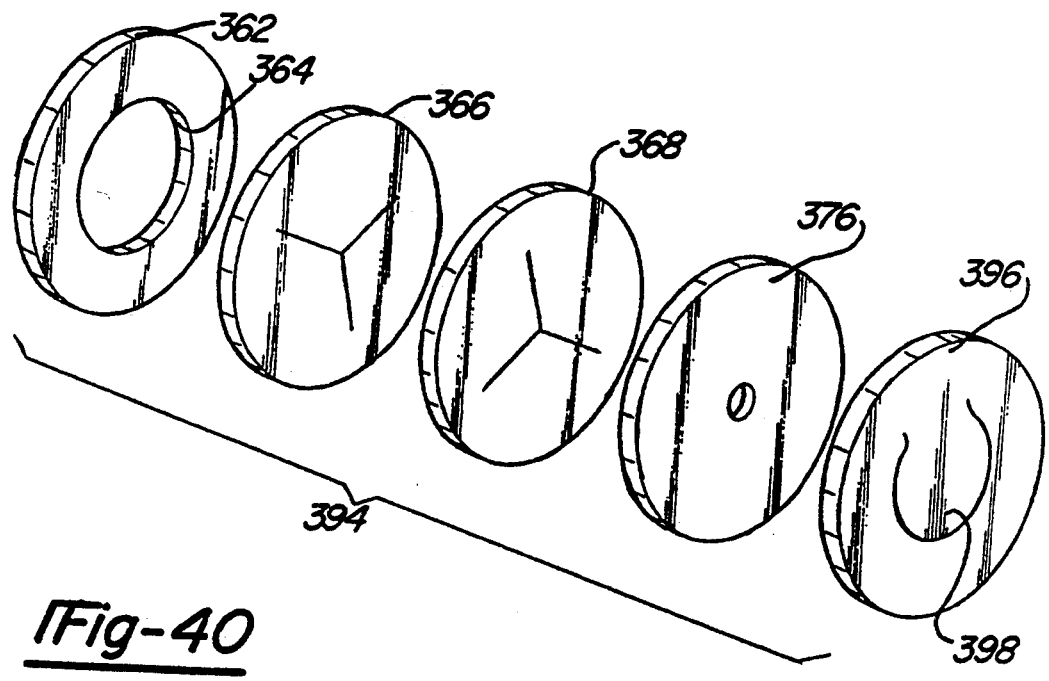
FIG. 40 is an exploded pictorial view of another alternate embodiment of an articulating valve according to this invention.

FIG. 40 shows yet another embodiment of valve assembly according to this invention and is designated by reference number 394. This embodiment also features a number of elements common to that of valve assembly 350 which are further identified by like reference numbers. Valve 394, however, features a flapper type valve element 396 having a central flap or leaf 398. Flapper valve 396 is provided to act as a check valve providing enhanced resistance to reverse fluid leakage since flap 398 is actuated by fluid pressure into sealing engagement with valve disc 376. Flap 398 is readily deflected upon the insertion of catheter 382 or another flexible introduced filament.

Figure 41:
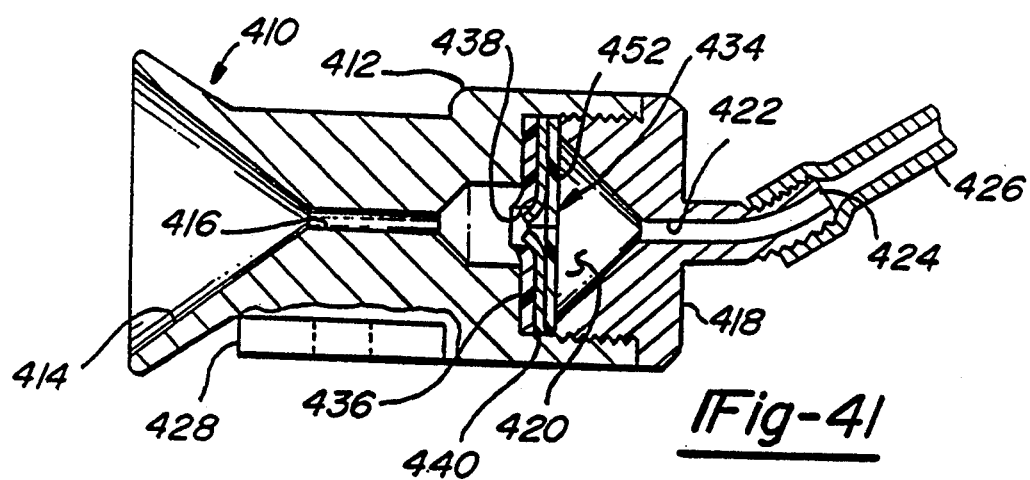
FIG. 41 is a cross-sectional view through an access port in accordance with a ninth embodiment of this invention shown in a normal condition in which an external filament is not present within the device.
Figure 42:
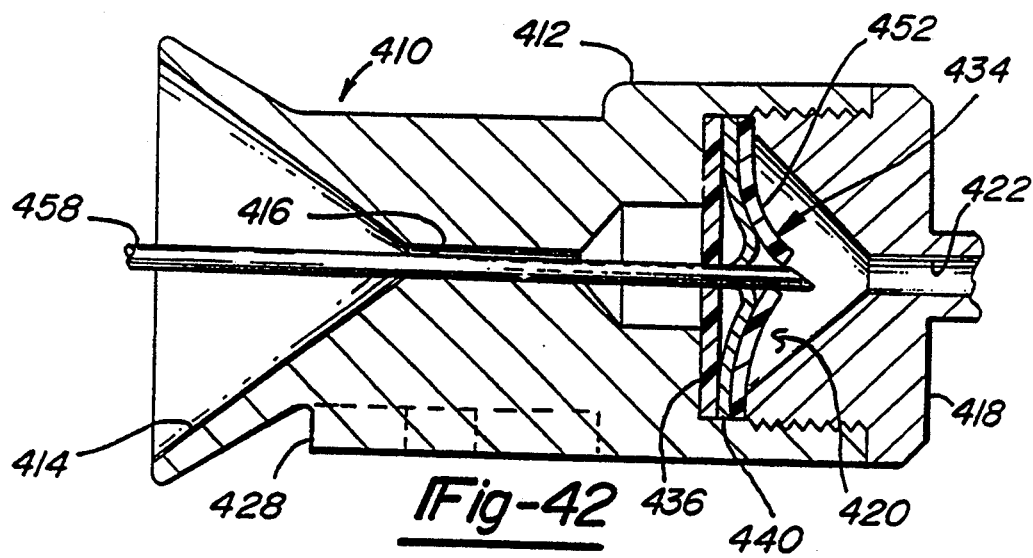
FIG. 42 is a somewhat enlarged cross-sectional view of the access port of FIG. 41 shown with an accessing needle penetrating the device.

An access port in accordance with a ninth embodiment of this invention is shown in FIGS. 41 and 42 and is generally designated by reference number 410. Access port 410 is designated to allow a sharp needle to access the device for purposes including infusing drugs or other fluids in the patient or withdrawing fluids from the patient. Access port 410 generally has housing 412 which defines a generally funnel shaped entrance orifice 414. Entrance orifice 414 has a decreasing cross-sectional area which ends at housing passageway 416. The shape of entrance orifice 414 serves to guide a needle into passageway 416. To that end, the surface of housing 412, forming orifice 414, is a hardened material, such as titanium, which has been found to be acceptable for this purpose.

Housing 412 together with outlet plug 418 define valve chamber 420 located between passageways 416 and 422. As shown, the protruding catheter connector tube 424 of outlet plug 418 is bent to provide a positive means for preventing an introduced needle from passing entirely through the device and potentially damaging a soft elastomeric implanted catheter 426. Connector tube 424 does, however, permit more flexible filaments, such as catheters, guide wires or optical fibers, to pass into implanted catheter 426. Mounting pad 428 enables the device to be conveniently mounted to subcutaneous support tissue, preferably but not exclusively using sutures, staples, or fasteners in general.

Figure 43:
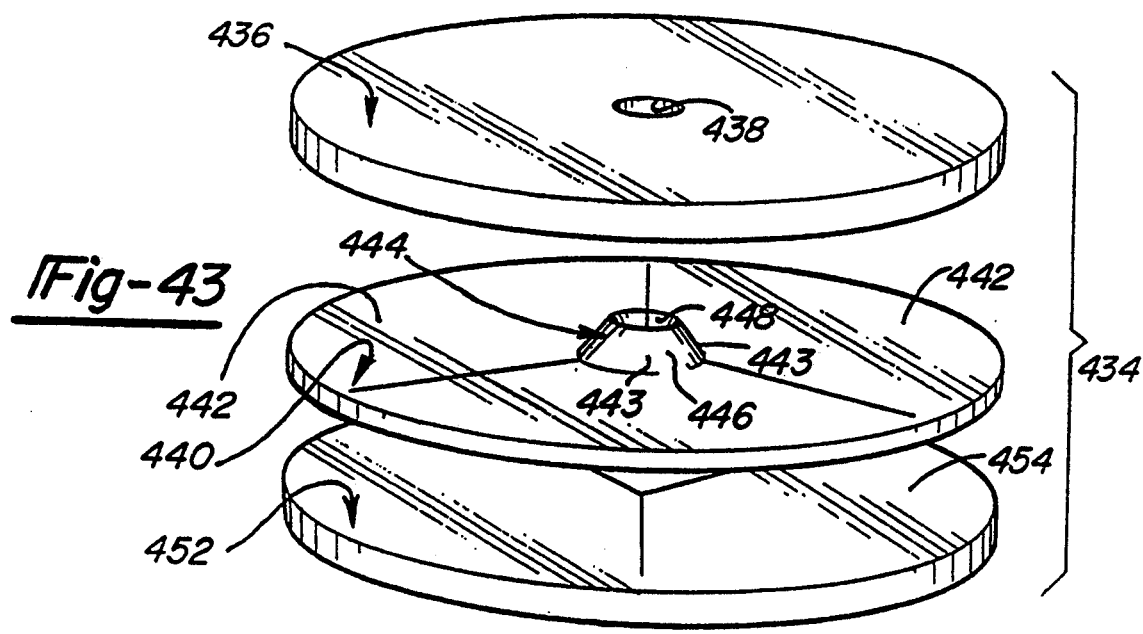
FIG. 43 is an exploded pictorial view of the valve assembly of the port shown in FIGS. 41 and 42.

Valve assembly 434 is disposed within valve chamber 420 and is best described with reference to FIG. 43. Valve disk 436 is made of an elastomeric material such as silicone rubber and is positioned in valve chamber 420 closest to entrance orifice 414. Disk 436 has a central aperture 438 defining a valve seat which is intended to seal against the introduced needle or filament upon insertion into access port 410, as will be described in more detail as follows. Stacked directly against disk 436 is sealing member 440 which is preferably made, at least partially, of a hard material such as a metal. Sealing member 440 as shown in FIGS. 41, 42, and 43 is a circular metal disk having three cuts intersecting at the center of the disk and extending radially to the outer perimeter but stopping short of the perimeter, thus defining three separate cantilever supported leaves 442. Each of leaves 42 is locally deflected from the plane of the disk at the disk center to define a segment 443 which combine to define conical sealing plug 444. Plug 444 has an external generally conical surface 446 with its center defining a concave surface 448. Sealing member 440 can be made from a flat sheet of metal stock which is locally deflected at the center area to define plug 444. Alternatively, the disk can be machined or cast such that the plug 444 is defined by a locally thickened region of the disk.

Valve assembly 434 also incorporates an additional leaflet valve element 452 formed from a flat sheet of elastomeric material. Valve element 452 defines radial cuts which join at the geometric center of the disk, defining separate valve leaves 454.

As shown in FIGS. 41 and 42, the three elements comprising valve assembly 434, namely valve disk 436, sealing member 440 and leaflet valve 452 are stacked directly against one another and are trapped in position between access port housing 412 and outlet plug 418. As shown in the Figures, housing 412 defines a relatively small diameter passageway on the side of valve assembly 434 closest to entrance passageway 416. In this manner, seal element 436 is constrained against deflecting toward entrance orifice 414 except at near its central area defining aperture 438. On the opposite side of valve assembly 434, outlet plug 418 defines a large diameter area for the deflection of the leaves of valve elements 440 and 452.

The operation and cooperation of the elements defining access port 410 will now be described with particular reference to FIGS. 41 and 42. FIG. 41 shows the configuration of valve assembly 434 when access port 410 is in its normal condition, implanted within the patient and not being used for access. In that condition, the segments of sealing member 440 making up sealing plug 444 project into and seal against disk aperture 438 which acts as a valve seat. Plug 444, having a conical outside surface 446, presses against disk aperture 438, causing it to be stretched and enlarged. Due to the contact between disk 436 and sealing member 440, a seal against fluid leakage is provided.

Leaflet valve element 452 is provided to enhance the level of sealing by preventing fluid leakage between sealing member leaves 442. In the normal condition of the device as shown in FIG. 41, the valve leaves 454 meet to provide a fluid seal. As shown in FIG. 43, as a means of providing enhanced fluid sealing, the orientation of the cuts defining leaflet valve leaves 454 and the cuts defining the individual sealing member leaves 442 are off-set or indexed so that they are not in registry.

FIG. 42 shows the orientation of the elements of access port 410 upon insertion of accessing external needle 58. Housing orifice 414 and passageway 416 serve to direct and orient needle 458 such that the sharp point of the needle strikes concave surface 448 of plug 444. Due to the enlargement of valve disk aperture 438 through its interaction with plug 444, the sharp point of the needle does not strike valve disk 436. As needle 458 is forced through the device, sealing member leaves 442 are forced to deflect in the direction of the outlet plug passageway 422. This movement of leaves 442 causes the segments defining plug 444 to move from engagement with disk aperture 438 which is allowed to contract in diameter. The undeformed diameter of aperture 438 is selected so that it will form a fluid seal against needle 458 (or another introduced filament such as a catheter, around the needle, which can be left in the device after the needle is removed). Continued deflection of leaves 442 allows free passage of the needle 458. Such deflections also causes valve leaves 454 to separate allowing passage of needle 458 without valve leaves 454 being damaged by contact with the needle point.

As is evident from the above description of the operation of access port 410, repeated access using needle 458 will not damage the device since the needle repeatedly strikes the hard material forming plug 444. Access port 410 also permits the introduction of other external filaments, such as an external catheter, optical fiber or guide wire, provided that it has sufficient rigidity to deflect the valve elements in the manner previously described. Access port 410 could also enable external filaments to be introduced via needle 458, either fed through its center passageway or introduced around the needle 458 like a typical angiography catheter.

Figure 45:
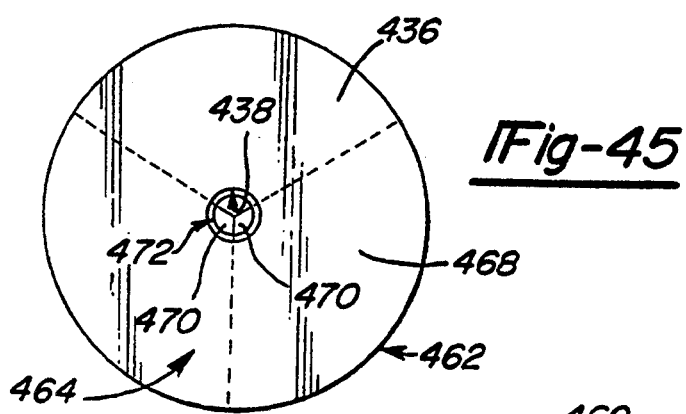
FIG. 45 is a frontal view of the valve assembly of the port shown in FIG. 44.
Figure 44:
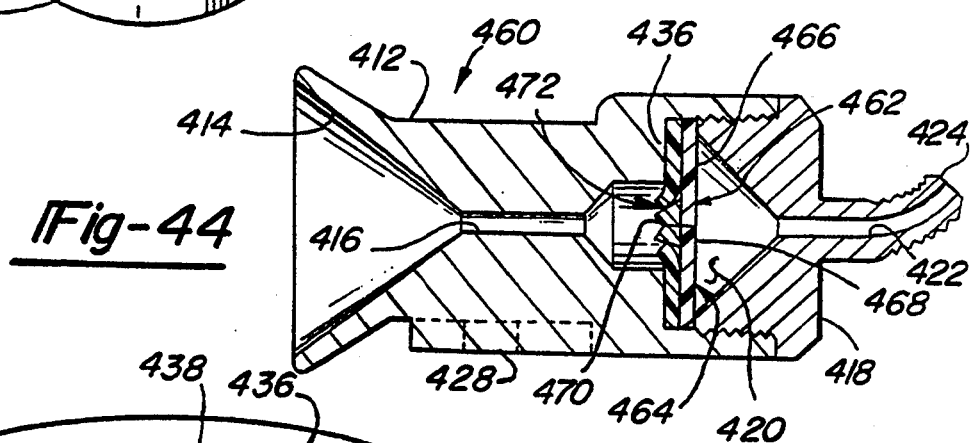
FIG. 44 is a cross-sectional view through an access port according to a tenth embodiment of this invention showing a valve assembly comprising metal seal elements affixed to a multi-leaf elastomeric valve disk.

FIG. 44 illustrates an access port 460 incorporating a valve assembly 462 in accordance with the tenth embodiment of this invention. This embodiment, along with those described elsewhere in this specification, has elements and features identical to those of the ninth embodiment which are identified with like reference numbers. FIG. 45 illustrates valve assembly 462 which includes a valve disk 436 identical to that previously described. The distinction of this embodiment over valve assembly 434 is that the sealing member 464 which defines plug 470 is a composite structure. Sealing element 464 is formed from an elastomeric or flexible base disk 466 having a number of radially projecting cuts defining individual leaves 468 as in the case of sealing member 440 described previously. Attached to leaves 468 near the center of base disk 466 are plug segments 470 which together define a sealing plug 472 as in the prior embodiment which are made of a hard material such as metal. Plug elements 470 are bonded or otherwise structurally affixed to disk 466.

In use, valve assembly 462 operates in a manner consistent with the description of valve assembly 434. A principal advantage of the configuration of valve assembly 462 is that sealing element disk 466 performs the combined functions of sealing, as with the leaflet vale element 452 of the first embodiment, and supporting plug segments 470.

Figure 46:
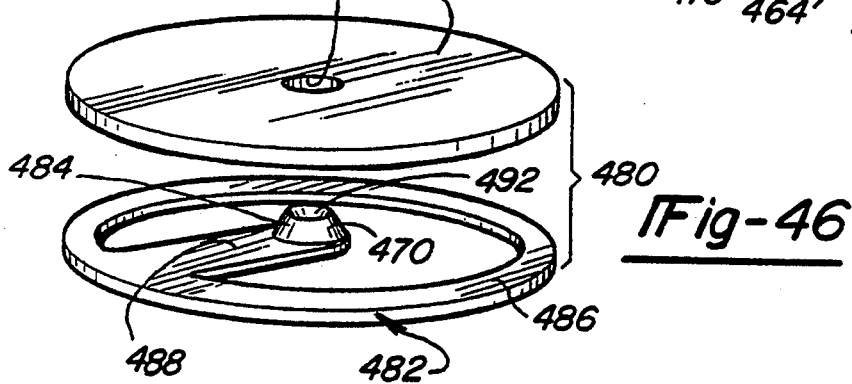
FIG. 46 is an exploded pictorial view of a valve assembly in accordance with an eleventh embodiment of this invention incorporating a unitary seal member for sealing against the valve seat formed by a sealing disk.
Figure 47:
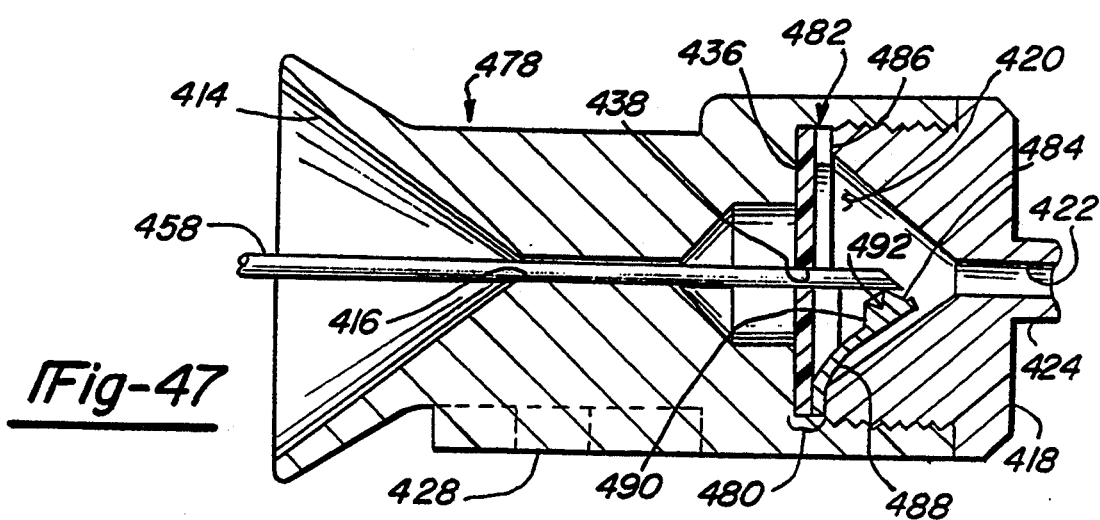
FIG. 47 is a cross-sectional view of an access port incorporating the valve assembly shown in FIG. 46 and further showing an accessing needle penetrating the device.

FIGS. 46 and 47 illustrate an access port 478 in accordance with an eleventh embodiment of this invention. Access port 478 has valve assembly 480 with a valve disk 436 identical to that present in the ninth and tenth embodiments. In this embodiment, however, sealing member 482 is a unitary structure which includes plug element 484 attached to a mounting ring 486 via a cantilever arm 488. As with the prior embodiments, plug 484 defines an external conical surface 490 and a central concave surface 492. In this design, however, the plug 484 is a unitary element.

In operation, valve assembly 480 operates as like those of the prior embodiments in that in a normal condition without an external filament inserted within the access device, plug 484 is in sealing engagement with disk aperture 438. Upon the introduction of an external filament such as needle 458, engagement between the needle and sealing plug 484 urges it out of engagement with disk aperture 438, and deflects it sufficiently to allow passage of the needle, as shown in FIG. 47. This process also results in the contraction of the diameter of aperture 438, causing it to constrict around the introduced filament. A significant benefit of valve assembly 480 results from the fact that plug 484 is a unitary structure and, therefore, does not inherently provide a fluid leakage path. In the normal condition, with plug 484 against disk aperture 438, a fluid seal is provided and, therefore, additional sealing elements, such as a leaflet valve 452 shown in the tenth embodiment, are unnecessary.

Figure 48:
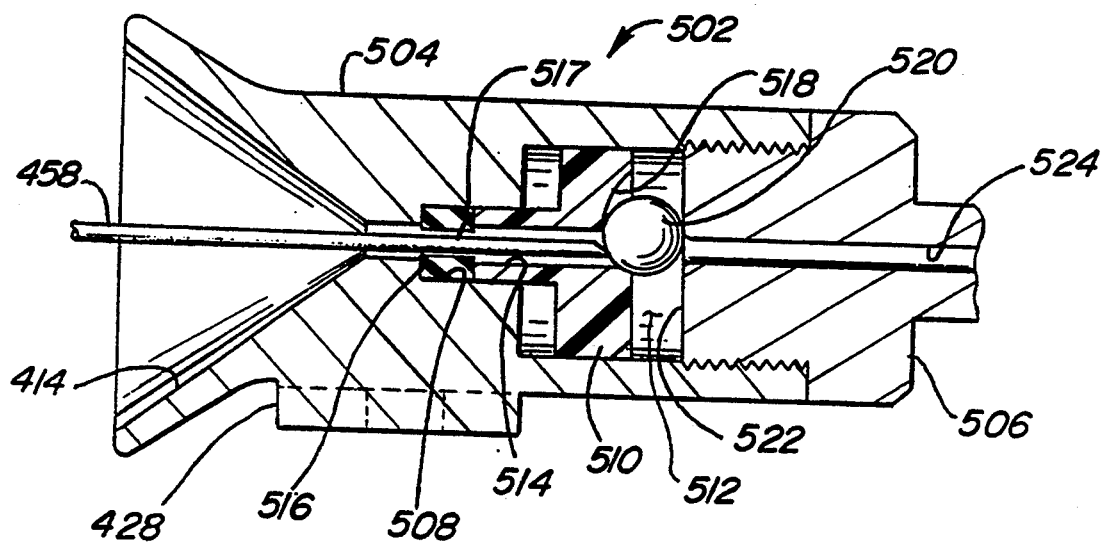
FIG. 48 is a cross-sectional view taken through an access port in accordance with a twelfth embodiment of this invention shown with a accessing needle partially penetrating the device.
Figure 49:
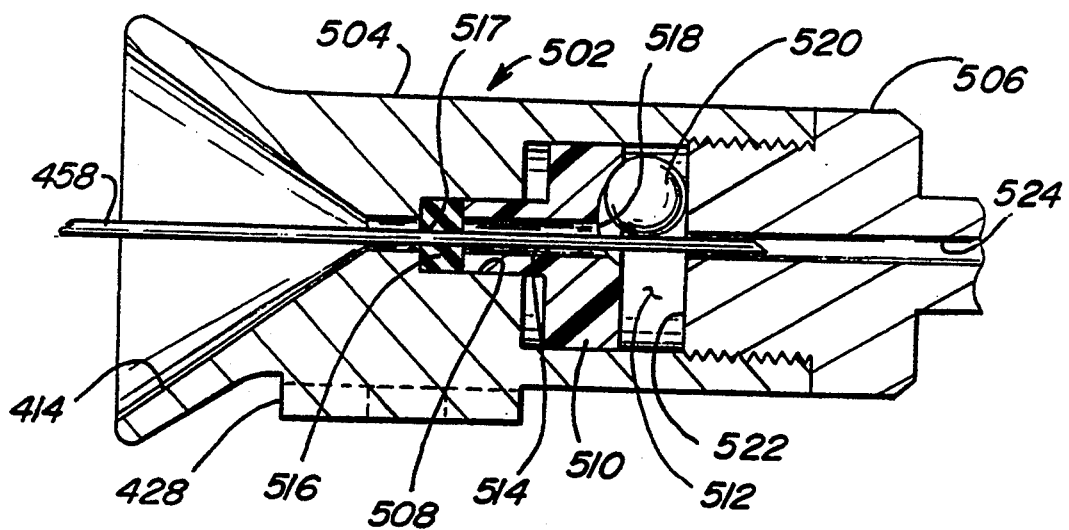
FIG. 49 is a cross-sectional view of the access port shown in FIG. 48 but showing the accessing needle penetrating the valve assembly to permit access to an implanted catheter.

FIGS. 48 and 49 provide an illustration of access port 502 in accordance with the twelfth embodiment of this invention. This embodiment features a modified housing 504 and outlet plug 506. Housing 504 forms a small diameter counter bore 508 extending toward entrance orifice 414. Piston element 510 is positioned within housing cavity 512 and includes a central filament passageway 514. Piston 510 butts against elastomeric bushing 516 having passageway 517, which is trapped within counterbore 508. The head of piston 510 forms a dished concave surface 518 which supports valve ball 520. Piston surface 518 is formed to position ball 520 such that it is displaced from alignment with piston passageway 514. Outlet plug 506 forms a generally flat surface 522 within housing cavity 512 which provides for movement of ball 520, as is described in more detail below.

Operation of access port 502 will be described with reference to FIGS. 48 and 49 FIG. 48 represents the orientation of the elements comprising the device while inserting access needle 458. As is shown in FIG. 48, access needle 458 engages ball 520 off-center. Continued insertion of needle 458 causes ball 520 to be displaced upward to the position shown in FIG. 49. During such displacement, piston 510 is caused to move toward entrance orifice 414 as ball 520 "rides out" of concave surface 518. This displacement of piston 510 compresses bushing 516. Since bushing 516 is trapped within counterbore 508 its axial compression causes bushing passageway 517 to constrict, thus causing it to seal against the introduced needle or other filament. As shown in FIG. 49, once ball 520 is fully displaced, free passage to the exit passageway 524 is provided. When needle 458 is completely removed from the device, ball 520 reseats in its position within concave surface 518 which provides a fluid seal. It would be possible to enhance the fluid seal provided by ball 520 in its normal position by utilizing an O-ring or other elastomeric valve seat (not shown) installed either on outlet plug 506 or a piston 510 and engaging the ball 520.

While the above description constitutes the preferred embodiments of the present invention, it will be appreciated that the various embodiments of the invention are susceptible of modification, variation and change, including the combining of various features from the several embodiments, without departing from the proper scope and fair meaning of the accompanying claims.

What is claimed is:

1. An implantable access device for permitting the access to a predetermined location within the body of a patient through an implanted internal catheter by a percutaneously placed filament such as a needle, external catheter, wire or optical fiber, said device being implantable within the body of the patient comprising:

a housing having a funnel shaped entrance orifice, a passageway and an exit orifice adapted for communication with the internal catheter, said entrance orifice having a decreasing cross sectional area defining a target area for insertion of said filament and causing said filament introduced into said entrance orifice to be directed to and enter said passageway, said passageway connecting said entrance orifice with said exit orifice, a valve means positioned within said housing and normally remaining closed for providing resistance to flow of fluids through said passageway, said valve means also permitting passage of said filament therethrough for enabling said filament to pass through said housing and communicate with said predetermined location, and means for supporting said access device within the body of the patient.

2. An implantable access device according to claim 1 wherein said entrance orifice is conical in shape.

3. An implantable access device as set forth in claim 2 wherein said entrance orifice includes a guide lip extending off of said entrance orifice increasing the size of said target area for insertion of said filament thereinto.

4. An implantable access device according to claim 1 wherein said entrance orifice includes a circular perimeter, said exit orifice being concentric with said circular perimeter.

5. An implantable access device according to claim 1 wherein said entrance orifice includes a circular perimeter, said exit orifice and said passageway being concentric with said circular perimeter.

6. An implantable access device according to claim 1 wherein said passageway and said exit orifice are coaxial.

7. An implantable access device according to claim 1 wherein said entrance orifice includes a perimeter defining a plane generally parallel with skin of said patient overlying said access device upon implantation of said access device within the body of the patient.

8. An implantable access device according to claim 1 wherein said valve means is an articulating valve designed for repeated engagement by said filament at a predetermined location.

9. An implantable access device according to claim 8 wherein said means is positioned within said passageway substantially adjacent to said entrance orifice.

10. An implantable access device according to claim 1 wherein said entrance orifice is formed by a surface of a hard material causing said filament contacting said surface to be directed toward said passageway.

11. An implantable access device according to claim 1 wherein said entrance orifice includes a recessed region defined therein increasing the area of said target area for the insertion of said filament thereinto.

12. An implantable access device according to claim 1 wherein said device comprises two spaced apart valve means defining a reservoir space therebetween.

13. An implantable access device according to claim 1 wherein said entrance orifice has a curved funnel shape.

14. An implantable access device according to claim 1 wherein said entrance orifice includes a guide lip extending off of said entrance orifice increasing said area of said target area for insertion of said filament thereinto.

15. An implantable access device according to claim 1 wherein said housing includes locating means which can be detected through external palpation after implantation of said device for determining the orientation of said entrance orifice.

16. An implantable access device according to claim 15 wherein said locating means is a projection on said housing.

17. An implantable access device according to claim 15 wherein said locating means is a recess in said housing.

18. An implantable access device according to claim 17 wherein said locating means includes recesses permitting external gripping of said device after implantation of said device during insertion of said filament.

19. An implantable access device according to claim 1 wherein said housing further includes portions at least partially defining a cavity for said valve means within said passageway with said valve means being positioned therein.

20. An implantable access device according to claim 19 wherein said device further comprises a plug, said plug engaging said housing and includes a surface cooperating with said housing to define said cavity.

21. An implantable access device according to claim 20 wherein said plug is threadably engaged with said housing.

22. An implantable access device according to claim 20 wherein said plug includes an exit passageway defining said exit orifice.

23. An implantable access device according to claim 22 wherein said plug includes an integrally formed exit tube, said exit passageway being defined therein.

24. An implantable access device according to claim 19 wherein said valve means is an articulating valve positioned within said cavity.

25. An implantable access device according to claim 24 wherein said cavity includes a first conical surface leading from said passageway generally to said valve means and a second conical surface leading from said valve means generally to said exit orifice.

26. An implantable access device according to claim 25 wherein said first conical surface is defined by a first cone angle and said second conical surface is defined by a second cone angle, said first cone angle being larger than said second cone angle.

27. An implantable access device according to claim 1 wherein said valve means is a leaflet valve having at least one generally flat disk of resilient material with at least one cut therethrough defining at least two leaves which are deflected upon insertion of said filament therethrough.

28. An implantable access device according to claim 27 wherein said housing constrains deflection of said leaves thereby inducing greater friction on said filament during withdrawal from said access device as compared with insertion of said filament into said access device.

29. An implantable access device according to claim 19 wherein said cavity is at least partially defined by a surface directing said filament toward said exit orifice.

30. An implantable access device according to claim 29 wherein said surface directing said filament toward said exit orifice is a conical surface.

31. An implantable access device according to claim 1 wherein said device further comprises stop means for limiting insertion of a relatively rigid filament through said device, said stop means permitting a flexible filament being more flexible than said relatively rigid filament to be further inserted through said device.

32. An implantable access device according to claim 31 wherein said stop means is formed in said passageway.

33. An implantable access device according to claim 32 wherein said stop means is a bend in said passageway.

34. An implantable access device according to claim 32 wherein said stop means is generally adjacent to said exit orifice.

35. An implantable access device according to claim 32 wherein said stop means is positioned between said entrance orifice and said valve means.

36. An implantable access device according to claim 1 wherein said housing includes a shield protecting said internal catheter from accidental contact with said filament as said filament is being inserted into the patient.

37. An access device being implantable within the body of a patient at a predetermined position for permitting access to an internal catheter by a flexible filament such as an external catheter, wire or optical fiber comprising:
  a housing defining an entrance orifice and an exit orifice adapted for communication with said internal catheter with said entrance orifice having a cross-sectional open area which decreases from said entrance orifice to a passageway communicating with said exit orifice, said entrance orifice causing said filament introduced into said entrance orifice to be directed toward and into said passageway,
  at least one articulating valve positioned within said housing which normally remains closed to provide resistance to flow of fluids through said valve, said valve permitting said filament to pass through said valve enabling said filament to pass through said housing and communicate with said internal catheter, said valve assembly further sealing around said filament when said filament is introduced through said valve and
  means for supporting said housing in a predetermined position within the body of a patient.

38. An implantable patient access device for permitting access to a predetermined location within the body of a patient through an implanted internal catheter by a percutaneously placed filament such as a needle, external catheter, wire or optical fiber comprising:
  a housing defining an entrance and a single exit orifice, adapted for communication with said internal catheter with said entrance orifice having a cross-sectional open area which decreases from said entrance orifice to a passageway communicating with said exit orifice, said entrance orifice causing said filament introduced into said entrance orifice to be directed toward and into said passageway and through said exit orifice,
  at least one articulating valve positioned within said housing passageway which normally remains closed to provide resistance to flow of fluids through said valve, yet opens to permit said filament to pass through said valve enabling said filament to communicate with said internal catheter through said exit orifice, and
  means for supporting said housing within the body of the patient.

39. A method for permitting repeated percutaneous access by a filament such as a needle, external catheter, wire or optical fiber, to preselected tissue within the body of a patient comprising the steps of:
  implanting within the body of the patient an access device having an funnel shaped entrance orifice, a passageway, an exit orifice, and an articulating valve which normally resists the flow of fluids through said passageway while allowing passage of said filament therethrough,
  providing an internal catheter and connecting said internal catheter to said access device at said exit orifice and positioning said internal catheter to communicate from the access device to said preselected tissue,
  providing said filament,
  inserting said filament percutaneously into said access device entrance orifice, and
  feeding said filament through said articulating valve and into said internal catheter, thereby providing said filament access to said preselected tissue.

40. A method for permitting repeated access to preselected tissue within the body of a patient by a rigid filament having a less rigid coaxial filament therewith comprising the steps of:
  implanting within the body of the patient an access device having an funnel shaped entrance orifice, a passageway, an internal cavity, an exit orifice, an articulating valve which normally resists the flow of fluids through said passageway, and limiting means for limiting the depth to which said rigid filament may be inserted into said device,
  providing an internal catheter and connecting said internal catheter to said access device at said exit orifice and positioning said internal catheter to communicate from said access device to said preselected tissue,
  providing said rigid and less rigid filaments,
  inserting said rigid and less rigid filaments percutaneously into said access device through said entrance orifice,
  withdrawing said rigid filament from said access device while retaining said less rigid filament within said access device, and
  further inserting said less rigid filament into said access device beyond said limiting means thereby providing access to said preselected tissue.

41. The method according to claim 40 wherein said rigid and less rigid filaments are inserted to a depth limited by said limiting means.

42. The method according to claim 40 wherein said limiting means is positioned between said entrance orifice and said valve.

43. The method according to claim 40 wherein said limiting means is positioned between said valve and said exit orifice.

44. A method for permitting repeated access by a wire to an internal catheter providing access to preselected tissue within the body of a patient, said method comprising the steps of:
  providing an implantable access device having a funnel shaped entrance orifice, a passageway, an exit orifice, and an articulating valve which normally resists the flow of fluids through said access device yet permits passage of said wire therethrough,
  providing an internal catheter and connecting said internal catheter to said access device at said exit orifice and positioning said internal catheter to communicate from said access device to said preselected tissue, providing said wire, inserting said wire percutaneously into and through said access device, and manipulating said wire to perform an intended function of said wire.

45. The method of claim 44 wherein said wire is a clearing wire and further comprising the steps of:

feeding said clearing wire through said valve and into said internal catheter, and manipulating said clearing wire to clear said internal catheter of accumulated deposits therein.

46. A method for permitting access by a guide wire to an internal catheter providing access to a preselected tissue within the body of a patient, said method comprising the steps of:

providing an implantable access device having an funnel shaped entrance orifice, a passageway, an exit orifice, and an articulating valve which normally resists the flow of fluids through said access device yet which permits passage of said guide wire therethrough, providing an internal catheter connected to said access device at said exit orifice and positioning said internal catheter to communicate from said access device to said preselected tissue, providing said guide wire, inserting said guide wire percutaneously into said access device through said entrance orifice, feeding said guide wire through said access device and into said internal catheter, and manipulating said guide wire to steer said guide wire within the body of the patient.

47. A method for locating an entrance to an access device implanted within the body of a patient and permitting repeated access to a preselected tissue within said patient by a filament such as a needle, external catheter, wire or optical fiber, said method comprising the steps of:

providing said implanted access device having a funnel shaped entrance orifice, indicia being provided on said device in a predetermined relation to said entrance orifice, said indicia indicating the orientation and position of said entrance orifice and being detectable through palpation, said access device further having a passageway, an exit orifice, and an articulating valve which normally resists the flow of fluids through said access device yet permits passage of said filament therethrough, providing an internal catheter and connecting said internal catheter to said access device at said exit orifice and positioning said internal catheter to communicate from said access device to said preselected tissue, performing palpation of said access device externally of said patient to locate said indicia, utilizing said indicia to determine the orientation and position of said entrance orifice relative to said patient, inserting said filament percutaneously into said entrance orifice, and feeding said filament through said access device and into said internal catheter thereby providing access to said preselected tissue.

48. An access device being implantable within the body of a patient for permitting access to an internal catheter by a filament such as a needle, external catheter, wire or optical fiber comprising:

a housing including a funnel shaped entrance orifice having a perimeter defining a target area for insertion of said filament, said housing also including an exit orifice and a passageway communicating said entrance orifice with said exit orifice, said entrance orifice having a decreasing cross-sectional area causing said filament introduced into said entrance orifice to be directed to and enter said passageway, said passageway being angularly oriented with respect to a normal line through a plane defined by said perimeter thereby causing said filament to undergo a bend, a barrier positioned within said housing and to provide resistance to flow of fluids through said device, said barrier permitting passage of said filament therethrough enabling said filament to communicate with said internal catheter, and a base configured for supporting said access device in a predetermined position within said body of said patient.

49. An implantable access device for permitting access to an internal catheter by a filament such as a needle, external catheter, wire or optical fiber, said device being implantable beneath the skin and within the body of a patient, said access device comprising:

a housing including a funnel shaped entrance orifice, a passageway and an exit orifice, said entrance orifice having a decreasing cross-sectional area defining a target area for insertion of said filament and causing said filament introduced into said entrance orifice to be directed to and enter said passageway, said passageway connecting said entrance orifice with said exit orifice;

a leaflet valve positioned within said passageway and normally remaining closed for providing resistance to flow of fluids through said passageway, said leaflet valve also permitting passage of said filament therethrough for enabling said filament to pass through said housing and communicate with said internal catheter, said leaflet valve including at least two resilient disks each having at least one slit formed therein, said slits of each of said disks being disaligned with one another; and means for supporting said access device in a predetermined position within said body of said patient.

50. An access port being implantable within the body of a patient for permitting access to an internal catheter by the percutaneous introduction of an external filament such as a catheter, needle, guide wire or optical fiber, said access device comprising:

a housing defining a funnel shaped entrance orifice and a single exit orifice, said entrance orifice having a cross-sectional open area which decreases in size to a passageway communicating with said exit orifice, said housing causing said filament introduced into said entrance orifice to be directed to enter said passageway, a leaflet valve assembly within said passageway and having at least one disk of resilient material, at least one slit through said disk defining two or more deflectable valve leaves, said valve assembly normally remaining closed to provide resistance to the flow of fluids through said valve assembly, said valve assembly opening to permit passage of said external filament inserted through said passageway and enabling said filament to pass through said housing and communicate with said internal catheter, and a support surface formed by said housing for enabling said housing to be supported within said body of said patient.

* * * * *

UNITED STATES PATENT AND TRADEMARK OFFICE
CERTIFICATE OF CORRECTION

PATENT NO.   : 5,356,381
DATED        : October 18, 1994
INVENTOR(S)  : William D. Ensminger, et al.

It is certified that error appears in the above-indentified patent and that said Letters Patent is hereby corrected as shown below:

Column 23, Line 48, Claim 9 after "said" insert --valve--.

Signed and Sealed this

Thirty-first Day of January, 1995

Attest:

BRUCE LEHMAN

Attesting Officer     Commissioner of Patents and Trademarks